US012740962B2

(12) United States Patent
Smitt

(10) Patent No.: US 12,740,962 B2
(45) Date of Patent: Sep. 22, 2026

(54) METHODS OF TREATING RESIDUAL BREAST CANCER WITH TRASTUZUMAB EMTANSINE

(71) Applicant: GENENTECH, INC., South San Francisco, CA (US)

(72) Inventor: Melanie Smitt, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 25 days.

(21) Appl. No.: 16/653,167

(22) Filed: Oct. 15, 2019

(65) Prior Publication Data

US 2020/0114018 A1 Apr. 16, 2020

Related U.S. Application Data

(60) Provisional application No. 62/922,229, filed on Apr. 24, 2019, provisional application No. 62/745,914, filed on Oct. 15, 2018.

(51) Int. Cl.

| | |
|---|---|
| ***A61K 47/68*** | (2017.01) |
| ***A61K 31/337*** | (2006.01) |
| ***A61K 31/537*** | (2006.01) |
| ***A61P 35/00*** | (2006.01) |

(52) U.S. Cl.

CPC .......... *A61K 31/337* (2013.01); *A61K 31/537* (2013.01); *A61K 47/68033* (2023.08); *A61K 47/6855* (2017.08); *A61P 35/00* (2018.01)

(58) Field of Classification Search

CPC .............. A61K 47/6855; A61K 31/337; A61K 31/537; A61K 47/6803; A61K 2039/505; A61K 2039/545; A61K 39/39558; A61K 45/06; A61K 2300/00; A61P 35/00; C07K 16/32

See application file for complete search history.

(56) References Cited

U.S. PATENT DOCUMENTS

| | | | | |
|---|---|---|---|---|
| 5,208,020 | A | 5/1993 | Chari et al. | |
| 5,677,171 | A | 10/1997 | Hudziak et al. | |
| 5,821,337 | A | 10/1998 | Carter et al. | |
| 6,054,297 | A | 4/2000 | Carter et al. | |
| 6,165,464 | A | 12/2000 | Hudziak et al. | |
| 6,339,142 | B1 | 1/2002 | Basey et al. | |
| 6,407,213 | B1 | 6/2002 | Carter et al. | |
| 6,441,163 | B1 | 8/2002 | Chari et al. | |
| 6,639,055 | B1 | 10/2003 | Carter et al. | |
| 6,719,971 | B1 | 4/2004 | Carter et al. | |
| 6,800,738 | B1 | 10/2004 | Carter et al. | |
| 7,074,404 | B2 | 7/2006 | Basey et al. | |
| 7,097,840 | B2 | 8/2006 | Erickson et al. | |
| 7,560,111 | B2 | 7/2009 | Kao et al. | |
| 11,406,715 | B2 * | 8/2022 | Guardino | A61P 35/04 |
| 2005/0166993 | A1 | 8/2005 | Viken et al. | |
| 2005/0276812 | A1 | 12/2005 | Ebens, Jr. et al. | |
| 2011/0165155 | A1 | 7/2011 | Agresta et al. | |

FOREIGN PATENT DOCUMENTS

| | | |
|---|---|---|
| WO | WO 2017/087280 A1 | 5/2017 |

OTHER PUBLICATIONS

Junttila et al, Breast Cancer Res Treat 128:347-356, 2011.*

Krop et al (Lancet Oncol, 15:689-699, 2014).*

Martinez et al, (Critical Reviews in Oncology/Hematology, 97:96-106, 2016).*

Symmans et al (J. Clin. Oncol. 25:4414-4422, 2007).*

Yan H et al. Efficacy and safety of trastuzumab emtansine (T-DM1) in the treatment of HER2-positive metastatic breast cancer (MBC): a meta-analysis of randomized controlled trial. Oncotarget. Nov. 24, 2017; 8(60): 102458-102467. (Year: 2017).*

Parker S et al. Clinical guidelines for the management of breast cancer. 2016 West Midlands Clinical Networks and Clinical Senate (https://www.england.nhs.uk/mids-east/wp-content/uploads/sites/7/2018/02/guidelines-for-the-management-of-breast-cancer-v1.pdf) (Year: 2016).*

Barok et al. Trastuzumab emtansine: mechanisms of action and drug resistance. Breast Cancer Research 2014, 16:209 1-12 (Year: 2014).*

Hoffmann-La Roche et al. (KATHERINE) Clinical Trials NCT01772472 (https://classic.clinicaltrials.gov/ct2/history/NCT01772472?V_131=View#StudyPageTop Oct. 12, 2017). (Year: 2017).*

Hoffmann-La Roche et al. NCT01772472 Protocol for Trastuzumab Emtansine (https://cdn.clinicaltrials.gov/large-docs/72/NCT01772472/Prot_000.pdf). (Year: 2015).*

Genentech KADCYLA® (ado-trastuzumab emtansine) prescribing information (https://www.accessdata.fda.gov/drugsatfda_docs/label/2016/125427s096lbl.pdf, Jul. 2016) (Year: 2016).*

Krop et al. Feasibility and Cardiac Safety of Trastuzumab Emtansine After Anthracycline-Based Chemotherapy as (neo)Adjuvant Therapy for Human Epidermal Growth Factor Receptor 2-Positive Early-Stage Breast Cancer. (Journal of Clinical Oncology, 2015 33(10:1136-1142 and supplemental protocol) (Year: 2015).*

Bayraktar S et al. Neoadjuvant dose-dense docetaxel, carboplatinum, and trastuzumab (ddTCH) chemotherapy for HER2 overexpressing breast cancer. (J Clin Oncol 2009 27 15_suppl e11557) (Year: 2009).*

Harper K et al. News in Brief: T-DM1 Reduces HER2+ Breast Cancer Recurrence. Cancer Discov (2019) 9 (2): 158-159 (Year: 2019).*

Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14:737-744 (1996).

Baselga et al., "Recombinant Humanized Anti-HER2 Antibody (HerceptinTM) Enhances the Antitumor Activity of Paclitaxel and Doxorubicin against HER2/neu Overexpressing Human Breast Cancer Xenografts," Cancer Res. 58:2825-2831 (1998).

(Continued)

*Primary Examiner* — Karen A. Canella
*Assistant Examiner* — John J Skoko, III
(74) *Attorney, Agent, or Firm* — Baker Botts L.L.P.

(57) ABSTRACT

Methods of treating patients having HER2-positive early breast cancer with the antibody-drug conjugate trastuzumab emtansine (T-DM1) are provided.

19 Claims, 12 Drawing Sheets

(56) References Cited

OTHER PUBLICATIONS

Cabanillas et al., "Results of a Phase II Study of Maytansine in Patients With Breast Carcinoma and Melanoma," Cancer Treat Rep, 63:507-509 (1979).
Cassady et al., "Recent Developments in the Maytansinoid Antitumor Agents," Chem Pharm Bull 52(1):1-26 (2004).
Cho et al., "Structure of the extracellular region of HER2 alone and in complex with the Herceptin Fab," Nature 421:756-760 (2003).
Cortazar et al., "Pathological complete response and long-term clinical benefit in breast cancer: the CTNeoBC pooled analysis," Lancet 384:164-172 (2014).
Coussens et al., "Tyrosine Kinase Receptor with Extensive Homology to EGF Receptor Shares Chromosomal Location with neu Oncogene," Science 230:1132-1139 (1985).
De Azambuja et al., "Lapatinib with trastuzumab for HER2-positive early breast cancer (NeoALTTO): survival outcomes of a randomised, open-label, multicentre, phase 3 trial: survival outcomes and their association with pathological complete response," Lancet Oncol 15:1137-1146 (2014).
Dieras et al., "Trastuzumab Emtansine in Human Epidermal Growth Factor Receptor 2-Positive Metastatic Breast Cancer: an Integrated Safety Analysis," J Clin Oncol. 32:2750-2757 (2014).
Dieras et al., "Trastuzumab emtansine versus capecitabine plus lapatinib in patients with previously treated HER2-positive advanced breast cancer (EMILIA): a descriptive analysis of final overall survival results from a randomised, open-label, phase 3 trial," Lancet Oncol 18(6):732-742 (2017).
Egloff et al., "Ado-Trastuzumab Emtansine-Induced Pulmonary Toxicity: A Single-Institution Retrospective Review," Case Rep Oncol 11:527-533 (2018).
Gianni et al., "5-year analysis of neoadjuvant pertuzumab and trastuzumab in patients with locally advanced, inflammatory, or early-stage HER2-positive breast cancer (NeoSphere): a multicentre, open-label, phase 2 randomised trial," Lancet Oncol 17:791-800 (2016).
Gianni et al., "Neoadjuvant and adjuvant trastuzumab in patients with HER2-positive locally advanced breast cancer (NOAH): follow-up of a randomized controlled superiority trial with a parallel HER2-negative cohort," Lancet Oncol 15:640-647 (2014).
Gullo et al., "Impact of timing of trastuzumab initiation on long-term outcome of patients with early-stage HER2-positive breast cancer: the "one thousand HER2 patients" project," Br J Cancer 119:374-380 (2018).
Harari et al., "Molecular mechanisms underlying ErbB2/HER2 action in breast cancer," Oncogene 19:6102-6114 (2000).
Hotaling et al., "The humanized anti-HER2 antibody rhuMAb HER2 mediates antibody dependent cell-mediated cytotoxicity via FcyR III," Proc. Annual Meeting Am Assoc Cancer Res 37:471, #3215 (1996).
Hudis et al., "Proposal for Standardized Definitions for Efficacy End Points in Adjuvant Breast Cancer Trials: the STEEP System," J Clin Oncol 25:2127-2132 (2007).
Hudziak et al., "p185HER2 Monoclonal Antibody Has Antiproliferative Effects In Vitro and Sensitizes Human Breast Tumor Cells to Tumor Necrosis Factor," Mol Cell Biol 9(3):1165-1172 (1989).
Hurvitz et al., "Neoadjuvant trastuzumab, pertuzumab, and chemotherapy versus trastuzumab emtansine plus pertuzumab in patients with HER2-positive breast cancer (KRISTINE): a randomised, open-label, multicentre, phase 3 trial," Lancet Oncol. 19:115-126 (2018).
Issell et al., "Maytansine," Cancer Treat. Rev. 5:199-207 (1978).
Jemal et al., "Global Cancer Statistics," CA Cancer J Clin, 61:69-90 (2011).
Junttila et al., "Trastuzumab-DM1 (T-DM1) retains all the mechanisms of action of trastuzumab and efficiently inhibits growth of lapatinib insensitive breast cancer," Breast Cancer Res Treat 128:347-356 (2011).
Kadcyla (package insert). South San Francisco, CA: Genentech, Inc.; Sep. 2018.
Krop et al., "Feasibility and Cardiac Safety of Trastuzumab Emtansine after Anthracycline-Based Chemotherapy as (neo)Adjuvant Therapy for Human Epidermal Growth Factor Receptor 2-Positive Early-Stage Breast Cancer," J Clin Oncol 33:1136-1142 (2015).
Krop et al., "Trastuzumab emtansine versus treatment of physician's choice for pretreated HER2-positive advanced breast cancer (TH3RESA): a randomised, open-label, phase 3 trial," Lancet Oncol 15:689-699 (2014).
Krop et al., "Trastuzumab emtansine versus treatment of physician's choice in patients with previously treated HER2-positive metastatic breast cancer (TH3RESA): final overall survival results from a randomised open-label phase 3 trial," Lancet Oncol 18:743-754 (2017).
Lewis et al., "Differential responses of human tumor cell lines to anti-p185HER2 monoclonal antibodies," Cancer Immunol Immunother 37:255-263 (1993).
Lewis et al., "Targeting HER2-Positive Breast Cancer with Trastuzumab-DM1, an Antibody-Cytotoxic Drug Conjugate," Cancer Res 68:9280-9290 (2008).
Lindstrom et al., "Clinically Used Breast Cancer Markers Such as Estrogen Receptor, Progesterone Receptor, and Human Epidermal Growth Factor Receptor 2 are Unstable throughout Tumor Progression," J Clin Oncol 30:2601-2608 (2012).
Malik et al., "Dose-Response Studies of Recombinant Humanized Monoclonal Antibody 2C4 in Tumor Xenograft Models," Am Soc Cancer Res 44: Abstract (2003).
Martin et al., "Neratinib after trastuzumab-based adjuvant therapy in HER2-positive breast cancer (ExteNET): 5-year analysis of a randomised, double-blind, placebo-controlled, phase 3 trial," Lancet Oncol 18:1688-1700 (2017).
Marty et al., "Randomized Phase II Trial of the Efficacy and Safety of Trastuzumab Combined with Docetaxel in Patients with Human Epidermal Growth Factor Receptor 2-Positive Metastatic Breast Cancer Administered as First-Line Treatment: The M77001 Study Group," J Clin Oncol 23:4265-4274 (2005).
Masuda et al., "Adjuvant Capecitabine for Breast Cancer after Preoperative Chemotherapy," N Engl J Med 376:2147-2159 (2017).
National Comprehensive Cancer Network. NCCN clinical practice guidelines in oncology: breast cancer version 1.2018 (Mar. 20, 2018).
Pegram et al., "Antibody dependent cell-mediated cytatoxicity in breast cancer patients in Phase III clinical trials of a humanized anti-HER2 antibody," Proc Am Assoc Cancer Res 38:602, #4044 (1997).
Perez et al., "Trastuzumab Emtansine With or Without Pertuzumab Versus Trastuzumab Plus Taxane for Human Epidermal Growth Factor Receptor 2-Positive, Advanced Breast Cancer: Primary Results from the Phase III Marianne Study," J Clin Oncol 35(2): 141-148 (2017).
Piccart-Gebhart et al., "Trastuzumab after Adjuvant Chemotherapy in HER2-Positive Breast Cancer," N Engl. J Med 353(16):1659-1672 (2005).
Press et al., "Her-2/neu Expression in Node-negative Breast Cancer: Direct Tissue Quantitation by Computerized Image Analysis and Association of Overexpression with Increased Risk of Recurrent Disease," Cancer Res 53:4960-4970 (1993).
Promberger et al., "Postoperative CMF Does Not Ameliorate Poor Outcomes in Women With Residual Invasive Breast Cancer after Neoadjuvant Epirubicin/Docetaxel Chemotherapy," Clin Breast Cancer 15:505-511 (2015).
Remillard et al., "Antimitotic Activity of the Potent Tumor Inhibitor Maytansine," Science 189:1002-1005 (1975).
Romond et al., "Trastuzumab plus Adjuvant Chemotherapy for Operable HER2-Positive Breast Cancer," The N Engl. J Med 353(16):1673-1684 (2005).
Schneeweiss et al., Long-term efficacy analysis of the randomised, phase II TRYPHAENA cardiac safety study: Evaluating pertuzumab and trastuzumab plus standard neoadjuvant anthracycline-containing and anthracycline-free chemotherapy regimens in patients with HER2-positive early breast cancer. Eur J Cancer 89:27-35 (2018).

(56) References Cited

OTHER PUBLICATIONS

Senkus et al., "Primary breast cancer: ESMO Clinical Practice Guidelines for diagnosis, treatment and follow-up," Ann Oncol 26(Suppl 5):v8-v30 (2015).
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Slamon et al., "Use of Chemotherapy Plus a Monoclonal Antibody Against HER2 for Metastatic Breast Cancer that Overexpresses HER2," New Engl. J. Med. 344(11):783-792 (2001).
Slamon et al., Expression of EGFR ligands betacellulin and tenascin C are associated with molecular response following gefitinib treatment in women with primary breast cancer, Breast Cancer Research and Treatment 100(Suppl. 1):S52 (2006).
Sliwkowski et al., "Nonclinical Studies Addressing the Mechanism of Action of Trastuzumab (Herceptin)," Seminars in Oncology 26(Suppl 12):60-70 (1999).
Sliwkowski, "Ready to partner," Nat Struct Biol 10(3):158-159 (2003).
Untch et al., "Pathologic Complete Response after Neoadjuvant Chemotherapy Plus Trastuzumab Predicts Favorable Survival in Human Epidermal Growth Factor Receptor 2-Overexpressing Breast Cancer: Results From the TECHNO Trial of the AGO and GBG Study Groups," J Clin Oncol 29:3351-3357 (2011).
Verma et al., "Trastuzumab Emtansine for HER2-Positive Advanced Breast Cancer," N Engl J Med 367:1783-1791 (2012).
Vogel et al., "Efficacy and Safety of Trastuzumab as a Single Agent in First-Line Treatment of HER2-Overexpressing Metastatic Breast Cancer," J Clin Oncol 20:719-726 (2002).
Von Minckwitz et al., "Adjuvant Pertuzumab and Trastuzumab in Early HER2-Positive Breast Cancer," N Engl J Med 377:122-131 (2017).
Von Minckwitz et al., "Trastuzumab Emtansine for Residual Invasive HER2-Positive Breast Cancer," N Engl J Med 380:617-628 (2019).
Yarden et al., "Untangling The ErbB Signalling Network," Nat Rev Mol Cell Biol 2:127-137 (2001).
Yoshida et al., "Change in HER2 Status after Neoadjuvant Chemotherapy and the Prognostic Impact in patients with primary breast cancer," J Surg Oncol 116:1021-1028 (2017).
Hicks, et al., "Trastuzumab as Adjuvant Therapy for Early Breast Cancer: The Importance of Accurate Human Epidermal Growth Factor Receptor 2 Testing", Archives of Pathology & Laboratory Medicine, 132(6):1008-1015 (2008).
Hoffmann-La Roche: "A Study of Trastuzumab Emtansine Versus Trastuzumab as Adjuvant Therapy in Patients With HER2-Positive Breast Cancer Who Have Residual Tumor in the Breast or Axillary Lymph Nodes Following Preoperative Therapy (KATHERINE)", Clinical Trials NCT01772472 (2013).
Martinez, et al., "Treatment of HER2 positive advanced breast cancer with T-DM1: A review of the literature", Critical Reviews in Oncology/Hematology, 97:96-106 (2016).
Extended European Search Report dated Aug. 17, 2023 in Application No. EP 22203622.
Hong et al., "Neoadjuvant Intratumoral Immunotherapy with TLR9 Activation and Anti-OxX40 Antibody Eradicates Metastatic Cancer," Cancer Research, 82(7):1396-1408 (2022).
Wedam et al., "FDA Approval Summary: Ado-Trastuzumab Emtansine for the Adjuvant Treatment of HER2-positive Early Breast Cancer," Clinical Cancer Research, 26(16):4180-4185 (2020).
"NCT01772472," Clinicaltrials. Gov Archive, vol. v135, JPN6022024939, Jul. 2018 (Jul. 1, 2018), ISSN: 0004966160.
Viani et al., "Adjuvant trastuzumab in the treatment of her-2-positive early breast cancer: a meta-analysis of published randomized trials," BMC Cancer 7:153 (2007) 11 pgs.
Tong et al., "Recent Advances in the Treatment of Breast Cancer," Frontiers in Oncology 8:227 (2018) 10 pgs.
"A Randomized, Multicenter, Open-Label Phase Iii Study to Evaluate the Efficacy and Safety of Trastuzumab Emtansine Versus Trastuzumab as Adjuvant Therapy for Patients With Her2-Positive Primary Breast Cancer Who Have Residual Tumor Present Pathologically in the Breast or Axillary Lymph Nodes Following Preoperative Therapy," NCT01772472, Protocol Version 6: Oct. 13, 2015, 121 pgs. URL: https://cdn.clinicaltrials.gov/large-docs/72/NCT01772472/Prot_000.pdf.

* cited by examiner

Radiation and endocrine therapy in accordance with protocol and local recommendations

| Characteristic | Trastuzumab (n=743) | T-DM1 (n=743) |
|---|---|---|
| Age — yr | | |
| Median | 49 | 49 |
| Age groups — no. of patients (%) | | |
| <40 years | 153 (20.6) | 143 (19.2) |
| 40-64 years | 522 (70.3) | 542 (72.9) |
| ≥65 years | 68 (9.2) | 58 (7.8) |
| Race — no. of patients (%) | | |
| White | 531 (71.5) | 551 (74.2) |
| Asian | 64 (8.6) | 65 (8.7) |
| Black or African American | 19 (2.6) | 21 (2.8) |
| American Indian* or Alaska Native | 50 (6.7) | 36 (4.8) |
| Multiple/unknown | 79 (10.6) | 70 (9.4) |
| Region — no. of patients (%) | | |
| North America | 164 (22.1) | 170 (22.9) |
| Western Europe | 403 (54.2) | 403 (54.2) |
| Rest of world | 176 (23.7) | 170 (22.9) |

FIG. 2A

| **Characteristic** | **Trastuzumab (n=743)** | **T-DM1 (n=743)** |
| --- | --- | --- |
| Primary tumor stage (at definitive surgery) — no. of patients (%) | | |
| ypT0, ypT1a, ypT1b, ypT1mic, ypTis | 306 (41.2) | 331 (44.5) |
| ypT1/ypT1c | 184 (24.8) | 175 (23.6) |
| ypT2 | 185 (24.9) | 174 (23.4) |
| ypT3 | 57 (7.7) | 51 (6.9) |
| ypT4, ypT4a, ypT4b, ypT4c | 9 (1.2) | 7 (0.9) |
| ypT4d | 1 (0.1) | 5 (0.7) |
| ypTX | 1 (0.1) | 0 |
| Regional lymph node stage (at definitive surgery) — no. of patients (%) | | |
| ypN0 | 335 (45.1) | 344 (46.3) |
| ypN1 | 213 (28.7) | 220 (29.6) |
| ypN2 | 103 (13.9) | 86 (11.6) |
| ypN3 | 30 (4.0) | 37 (5.0) |
| ypNX | 62 (8.3) | 56 (7.5) |
| | | |

FIG. 2B

| Characteristic | Trastuzumab (n=743) | T-DM1 (n=743) |
|---|---|---|
| Clinical stage at presentation — no. of patients (%) | | |
| Inoperable (stage T4NxM0 or TxN2–3M0) | 190 (25.6) | 185 (24.9) |
| Operable (stages T1-3N0–1M0) | 553 (74.4) | 558 (75.1) |
| Hormone-receptor status — no. of patients (%) | | |
| Positive (estrogen receptor and/or progesterone receptor) | 540 (72.7) | 534 (71.9) |
| Negative/unknown | 203 (27.3) | 209 (28.1) |
| Prior anthracycline — no. of patients (%) | 564 (75.9) | 579 (77.9) |
| Neoadjuvant HER2-targeted therapy — no. of patients (%) | | |
| Trastuzumab alone | 596 (80.2) | 600 (80.8) |
| Trastuzumab plus pertuzumab | 139 (18.7) | 133 (17.9) |
| Trastuzumab plus other HER2-targeted therapy† | 8 (1.1) | 10 (1.3) |
| Pathologic nodal status evaluated after neoadjuvant therapy — no. of patients (%) | | |
| Node positive | 346 (46.6) | 343 (46.2) |
| Node negative/not done | 397 (53.4) | 400 (53.8) |

FIG. 2C

| Event | Trastuzumab (n=743) | T-DM1 (n=743) |
|---|---|---|
| | *no. of patients (%)* | |
| Any invasive-disease event[†] | 165 (22.2) | 91 (12.2) |
| Category of first invasive-disease event | | |
| Distant recurrence | 118 (15.9) | 78 (10.5) |
| Central nervous system recurrence | 32 (4.3) | 44 (5.9) |
| Locoregional recurrence | 34 (4.6) | 8 (1.1) |
| Contralateral breast cancer | 10 (1.3) | 3 (0.4) |
| Death without previous event | 3 (0.4) | 2 (0.3) |

FIG. 4B

| End Point | Trastuzumab (n=743) | T-DM1 (n=743) |
|---|---|---|
| **Invasive-disease–free survival (STEEP definition)** | | |
| Patients with an event— no. of patients (%) | 167 (22.5) | 95 (12.8) |
| 3-year event-free rate—% (95% CI) | 76.9 (73.7–80.1) | 87.7 (85.2–90.2) |
| Hazard ratio (95% CI) | 0.51 (0.40–0.66) | |
| **Disease-free survival** | | |
| Patients with an event— no. of patients (%) | 167 (22.5) | 98 (13.2) |
| 3-year event-free rate—% (95% CI) | 76.9 (73.6–80.1) | 87.4 (84.9–89.9) |
| Hazard ratio (95% CI) | 0.53 (0.41–0.68) | |
| **Distant recurrence-free interval** | | |
| Patients with an event— no. of patients (%) | 121 (16.3) | 78 (10.5) |
| 3-year event-free rate—% (95% CI) | 83.0 (80.1–85.9) | 89.7 (87.4–92.0) |
| Hazard ratio (95% CI) | 0.60 (0.45–0.79) | |
| **Overall survival** | | |
| Patients with an event— no. of patients (%) | 56 (7.5) | 42 (5.7) |
| Hazard ratio (95% CI) | 0.70 (0.47–1.05) | |
| P-value (log-rank)‡ | 0.0848 | |

CI denotes confidence interval, STEEP denotes standardized efficacy end points, T-DM1 denotes trastuzumab emtansine.

FIG. 5

| Neoadjuvant therapy | Trastuzumab arm | T-DM1 arm |
|---|---|---|
| | IDFS events (events/no. patients) | |
| No prior P | 23.7% (141/596) | 13.0% (78/600) |
| | Unstratified HR=0.489 (95% CI, 0.371–0.645) | |
| | 3-year IDFS | |
| | 75.9% | 87.7% |
| Prior P | IDFS events (events/no. patients) | |
| | 17.3% (24/139) | 9.0% (12/133) |
| | Unstratified HR=0.498 (95% CI, 0.249–0.995) | |
| | 3-year IDFS | |
| | 80.9% | 91.4% |

*CI denotes confidence interval, HER2 human epidermal growth factor receptor 2, HR hazard ratio, IDFS invasive disease-free survival, P pertuzumab, and T-DM1 trastuzumab emtansine.

FIG. 7

METHODS OF TREATING RESIDUAL BREAST CANCER WITH TRASTUZUMAB EMTANSINE

CROSS REFERENCE TO RELATED APPLICATIONS

This application claims the benefit of U.S. Provisional Application No. 62/922,229, filed Apr. 24, 2019, and claims the benefit of U.S. Provisional Application No. 62/745,914, filed Oct. 15, 2018, the disclosures of all of which are incorporated herein by reference in their entireties.

FIELD OF THE INVENTION

The present disclosure relates to methods of using trastuzumab emtansine (T-DM1) for the treatment of residual breast cancer.

BACKGROUND OF THE INVENTION

Breast cancer is a highly significant cause of morbidity and mortality worldwide. There are over 1.3 million cases of breast cancer diagnosed globally each year with more than 450,000 deaths related to the disease (Jemal A, Bray F, Center M, et al. Global cancer statistics. CA Cancer J Clin, 2011; 61(2):69-90).

The HER2 (ErbB2) receptor tyrosine kinase is a member of the epidermal growth factor receptor (EGFR) family of transmembrane receptors. Overexpression of HER2 is observed in approximately 20% of human breast cancers (hereinafter referred to as HER2-positive breast cancer) and is implicated in the aggressive growth and poor clinical outcomes associated with these tumors (Slamon et al (1987) Science 235:177-182). HER2 protein overexpression can be determined using an immunohistochemistry based assessment of fixed tumor blocks (Press M F, et al (1993) Cancer Res 53:4960-70).

Trastuzumab (CAS 180288-69-1, HERCEPTIN®, huMAb4D5-8, rhuMAb HER2, Genentech) is a recombinant DNA-derived, IgG1 kappa, monoclonal antibody that is a humanized version of a murine anti-HER2 antibody (4D5) that selectively binds with high affinity in a cell-based assay (Kd=5 nM) to the extracellular domain of HER2 (U.S. Pat. Nos. 5,677,171; 5,821,337; 6,054,297; 6,165,464; 6,339,142; 6,407,213; 6,639,055; 6,719,971; 6,800,738; 7,074,404; Coussens et al (1985) Science 230:1132-9; Slamon et al (1989) Science 244:707-12; Slamon et al (2001) New Engl. J. Med. 344:783-792). Trastuzumab has been shown, in both in vitro assays and in animals, to inhibit the proliferation of human tumor cells that overexpress HER2 (Hudziak et al (1989) Mol Cell Biol 9:1165-72; Lewis et al (1993) Cancer Immunol Immunother; 37:255-63; Baselga et al (1998) Cancer Res. 58:2825-2831). Trastuzumab is a mediator of antibody-dependent cellular cytotoxicity, ADCC (Lewis et al (1993) Cancer Immunol Immunother 37(4): 255-263; Hotaling et al (1996) Proc. Annual Meeting Am Assoc Cancer Res; 37:471; Pegram M D, et al (1997) [Proc Am Assoc Cancer Res; 38:602; Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137).

HERCEPTIN® was approved in 1998 for the treatment of patients with HER2-overexpressing metastatic breast cancers (Baselga et al, (1996) J. Clin. Oncol. 14:737-744) that have received extensive prior anti-cancer therapy, and has since been used in over 300,000 patients (Slamon D J, et al. N Engl J Med 2001; 344:783-92; Vogel C L, et al. J Clin Oncol 2002; 20:719-26; Marty M, et al. J Clin Oncol 2005; 23:4265-74; Romond E H, et al. T N Engl J Med 2005; 353:1673-84; Piccart-Gebhart M J, et al. N Engl J Med 2005; 353:1659-72; Slamon D, et al. Breast Cancer Res Treat 2006, 100 (Suppl 1): 52). In 2006, the FDA approved HERCEPTIN® (Trastuzumab, Genentech Inc.) as part of a treatment regimen containing doxorubicin, cyclophosphamide and paclitaxel for the adjuvant treatment of patients with HER2-positive, node-positive breast cancer.

An alternative approach to antibody-targeted therapy is to utilize antibodies for delivery of cytotoxic drugs specifically to antigen-expressing cancer cells. Antibody-drug conjugates, or ADCs, are monoclonal antibodies to which highly potent cytotoxic agents have been conjugated. ADCs represent a novel approach to conferring tumor selectivity on systemically administered anti-tumor therapeutics. Utilizing surface antigens that are tumor-specific and/or overexpressed, ADCs are designed to focus the delivery of highly potent cytotoxic agents to tumor cells. The potential of this approach is to create a more favorable therapeutic window for such agents than could be achieved by their administration as free drugs.

Maytansinoids, derivatives of the anti-mitotic drug maytansine, bind to microtubules in a manner similar to vinca alkaloid drugs (Issell B F et al (1978) Cancer Treat. Rev. 5:199-207; Cabanillas F et al. (1979) Cancer Treat Rep, 63:507-9. DM1 is a thiol-containing maytansinoid derived from the naturally occurring ester ansamitocin P3 (Remillard S, Rebhun L I, Howie G A, et al. (1975) Science 189(4207):1002-1005.3; Cassady J M, Chan K K, Floss H G. (2004) Chem Pharm Bull 52(1):1-26.4). The related plant ester, maytansine, has been studied as a chemotherapeutic agent in approximately 800 patients, administered at a dose of 2.0 $mg/m^2$ every 3 weeks either as a single dose or for 3 consecutive days (Issell B F, Crooke S T. (1978) Maytansine. Cancer Treat Rev 5:199-207). Despite preclinical activity, the activity of maytansine in the clinic was modest at doses that could be safely delivered. The dose-limiting toxicity (DLT) was gastrointestinal, consisting of nausea, vomiting, and diarrhea (often followed by constipation). These toxicities were dose dependent but not schedule dependent. Peripheral neuropathy (predominantly sensory) was reported and was most apparent in patients with pre-existing neuropathy. Subclinical transient elevations of hepatic transaminase, alkaline phosphatase, and total bilirubin were reported. Constitutional toxicities, including weakness, lethargy, dysphoria, and insomnia, were common. Less common toxicities included infusion-site phlebitis and mild myelosuppression. Further development of the drug was abandoned in the 1980s because of the narrow therapeutic window.

Trastuzumab emtansine (T-DM1, Trastuzumab-MCC-DM1, ado-trastuzumab emtansine, KADCYLA®), a novel antibody-drug conjugate (ADC) for the treatment of HER2-positive breast cancer, is composed of the cytotoxic agent DM1 (a thiol-containing maytansinoid anti-microtubule agent) conjugated to trastuzumab at lysine side chains via an MCC linker, with an average drug load (drug to antibody ratio) of about 3.5. After binding to HER2 expressed on tumor cells, T-DM1 undergoes receptor-mediated internalization, resulting in intracellular release of cytotoxic catabolites containing DM1 and subsequent cell death.

Currently, patients with HER2-positive early breast cancer who do not achieve pathologic complete response with neoadjuvant treatment consisting of standard chemotherapy and HER2 targeted therapy are at a significantly higher risk of disease recurrence and decreased survival than those who attain a pathologic complete response. In HER2-positive patients, attaining a pathologic complete response is associated with a 62% to 73% reduction in risk of invasive disease or death and a 65% reduction in risk of death from any cause after 3 years (Schneeweiss 2018; de Azambuja Lancet Oncol 2014; Gianni Lancet Oncol 2014). However, pathologic complete response is achieved by only approximately 30% to 40% of these patients (Schneeweiss 2018; de Azambuja Lancet Oncol 2014; Gianni Lancet Oncol 2014; Untch J C O 2011). Accordingly, there remains an unmet medical need for treating those cancer patients who do not achieve pathologic complete response to neoadjuvant treatment.

SUMMARY OF THE INVENTION

The present disclosure relates generally to methods of treating breast cancer patients with the antibody-drug conjugate, trastuzumab emtansine (T-DM1).

In one aspect, the present disclosure concerns a method of adjuvant therapy comprising administering to a patient with HER2-positive early breast cancer an effective amount of trastuzumab emtansine (T-DM1) as a monotherapy, wherein the patient has residual disease after a pre-operative systemic treatment. In certain embodiments, the residual disease is present in a breast, in a lymph node, or present in a breast and a lymph node. In certain embodiments, the pre-operative systemic treatment comprises a HER2 targeted therapy, such as trastuzumab. In certain embodiments, the HER2 targeted therapy further comprises pertuzumab, lapatinib, neratinib, dacomitinib and/or afatinib. In certain embodiments, the HER2 targeted therapy comprises trastuzumab and pertuzumab. In certain embodiments, the HER2 targeted therapy comprises trastuzumab and further comprises an agent selected from the group consisting of lapatinib, neratinib, dacomitinib and afatinib. In certain embodiments, the pre-operative systemic treatment further comprises a taxane. In certain embodiments, the patient is an adult patient. In certain embodiments, the patient is subjected to a definitive surgery prior to the administration of T-DM1. In certain embodiments, the patient is administered T-DM1 no more than 12 weeks after the definitive surgery. In certain embodiments, the patient has completed at least 16 weeks of pre-operative systemic treatment with a taxane-containing chemotherapy regimen and HER2 targeted therapy. In certain embodiments, the patient has completed at least 6 cycles of taxane-containing chemotherapy. In certain embodiments, the patient is administered T-DM1 at a dose of 3.6 mg/kg every 3 weeks. In certain embodiments, the patient is administered T-DM1 for fourteen cycles at a dose of 3.6 mg/kg every 3 weeks. In certain embodiments, the adjuvant therapy substantially increases invasive disease-free survival (IDFS) as compared to adjuvant therapy with trastuzumab. In certain embodiments, the adjuvant therapy provides a 50% reduction in the risk of invasive disease recurrence as compared to adjuvant therapy with trastuzumab. In certain embodiments, the adjuvant therapy leads to a decrease in distant recurrence as compared to adjuvant therapy with trastuzumab. In certain embodiments, the adjuvant therapy provides a 40% reduction in the risk of distant recurrence as compared to adjuvant trastuzumab.

In one aspect, the present disclosure concerns trastuzumab emtansine (T-DM1) for use in an adjuvant therapy of HER2-positive early breast cancer in a patient, wherein the adjuvant therapy is a monotherapy and wherein the patient has residual disease after a pre-operative systemic treatment. In certain embodiments, the residual disease is present in a breast, present in a lymph node, or present in a breast and a lymph node. In certain embodiments, the pre-operative systemic treatment comprises a HER2 targeted therapy. In certain embodiments, the HER2 targeted therapy comprises trastuzumab. In certain embodiments, the HER2 targeted therapy further comprises pertuzumab, lapatinib, neratinib, dacomitinib and/or afatinib. In certain embodiments, the HER2 targeted therapy comprises trastuzumab and pertuzumab. In certain embodiments, the HER2 targeted therapy comprises trastuzumab and further comprises an agent selected from the group consisting of lapatinib, neratinib, dacomitinib and afatinib. In certain embodiments, the pre-operative systemic treatment further comprises a taxane. In certain embodiments, the patient is an adult patient. In certain embodiments, the patient is subjected to a definitive surgery prior to the administration of T-DM1. In certain embodiments, the adjuvant therapy substantially increases invasive disease-free survival (IDFS) as compared to adjuvant therapy with trastuzumab. In certain embodiments, the adjuvant therapy provides a 50% reduction in the risk of invasive disease recurrence as compared to adjuvant therapy with trastuzumab. In certain embodiments, the adjuvant therapy leads to a decrease in distant recurrence as compared to adjuvant therapy with trastuzumab. In certain embodiments, the adjuvant therapy provides a 40% reduction in the risk of distant recurrence as compared to adjuvant trastuzumab.

In one aspect, the present disclosure concerns the use of trastuzumab emtansine (T-DM1) in the manufacture of a medicament for use in an adjuvant therapy of HER2-positive early breast cancer in a patient, wherein the adjuvant therapy is a monotherapy and wherein the patient has residual disease after a pre-operative systemic treatment. In certain embodiments, the residual disease is present in a breast, present in a lymph node, or present in a breast and a lymph node. In certain embodiments, the pre-operative systemic treatment comprises a HER2 targeted therapy. In certain embodiments, the HER2 targeted therapy comprises trastuzumab. In certain embodiments, the HER2 targeted therapy further comprises pertuzumab, lapatinib, neratinib, dacomitinib and/or afatinib. In certain embodiments, the HER2 targeted therapy comprises trastuzumab and pertuzumab. In certain embodiments, the HER2 targeted therapy comprises trastuzumab and further comprises an agent selected from the group consisting of lapatinib, neratinib, dacomitinib and afatinib. In certain embodiments, the pre-operative systemic treatment further comprises a taxane. In certain embodiments, the patient is an adult patient. In certain embodiments, the patient is subjected to a definitive surgery prior to the administration of T-DM1. In certain embodiments, the adjuvant therapy substantially increases invasive disease-free survival (IDFS) as compared to adjuvant therapy with trastuzumab. In certain embodiments, the adjuvant therapy provides a 50% reduction in the risk of invasive disease recurrence as compared to adjuvant therapy with trastuzumab. In certain embodiments, the adjuvant therapy leads to a decrease in distant recurrence as compared to adjuvant therapy with trastuzumab. In certain embodiments, the adjuvant therapy provides a 40% reduction in the risk of distant recurrence as compared to adjuvant trastuzumab.

In one aspect, the present disclosure concerns a method for the treatment of breast cancer in a patient with HER2-positive early breast cancer who has residual disease in the breast or axillary lymph nodes after neoadjuvant therapy with chemotherapy and HER2 targeted therapy comprising (i) removing all clinically evident tumor cells in the breast and axillary lymph nodes by definitive surgery; and (ii) subjecting the patient to adjuvant treatment with T-DM1 in the absence of prior or concurrent adjuvant treatment with chemotherapy. In certain embodiments, the patient has residual disease in the breast or axillary lymph nodes after neoadjuvant therapy with a taxane and HER2 targeted therapy. In certain embodiments, the patient has completed at least 16 weeks of neoadjuvant therapy with a taxane-containing chemotherapy regimen and HER2 targeted therapy. In certain embodiments, the patient has completed at least 6 cycles of a taxane-containing chemotherapy regimen. In certain embodiments, the patient is subjected to adjuvant treatment with T-DM1 no more than 12 weeks after definitive surgery. In certain embodiments, the definitive surgery is performed at least 14 days following the completion of neoadjuvant therapy. In certain embodiments, definitive surgery is performed no later than 9 weeks following the completion of neoadjuvant therapy. In certain embodiments, the patient is subjected to adjuvant treatment with an infusion of T-DM1 at a dose of 3.6 mg/kg every 3 weeks. In certain embodiments, the patient is subjected to adjuvant treatment for fourteen cycles of an infusion of T-DM1 at a dose of 3.6 mg/kg every 3 weeks. In certain embodiments, the treatment substantially increases invasive disease-free survival (IDFS) as compared to adjuvant treatment with trastuzumab. In certain embodiments, the treatment leads to a decrease in distant recurrence as compared to adjuvant treatment with trastuzumab. In certain embodiments, the adjuvant therapy provides a 50% reduction in the risk of invasive disease recurrence as compared to adjuvant therapy with trastuzumab. In certain embodiments, the adjuvant therapy provides a 40% reduction in the risk of distant recurrence as compared to adjuvant trastuzumab.

In one aspect, the present disclosure concerns a method for the treatment of HER2-positive early breast cancer in a patient with residual disease following neoadjuvant therapy, the method comprising administrating to the patient an effective amount of T-DM1 after the patient is subjected to definitive surgery. In one aspect, the residual disease is a pathological residual invasive disease. In certain embodiments, the residual disease is a pathological residual invasive disease in the breast and/or axillary node. In certain embodiments, the method does not comprise prior or concurrent adjuvant treatment with chemotherapy. In certain embodiments, the neoadjuvant therapy comprises a taxane and HER2 targeted therapy. In certain embodiments, the neoadjuvant therapy comprises a taxane and trastuzumab. In certain embodiments, the patient has completed at least 16 weeks of neoadjuvant therapy. In certain embodiments, the patient has completed at least 6 cycles of taxane-containing neoadjuvant chemotherapy. In certain embodiments, the patient is subjected to treatment with T-DM1 no more than 12 weeks after definitive surgery. In certain embodiments, the definitive surgery is performed at least 14 days following the completion of neoadjuvant therapy. In certain embodiments, the definitive surgery is performed no later than 9 weeks following the completion of neoadjuvant therapy. In certain embodiments, the patient is subjected to treatment with an infusion of T-DM1 at a dose of 3.6 mg/kg every 3 weeks. In certain embodiments, the patient is subjected to treatment for fourteen cycles of an infusion of T-DM1 at a dose of 3.6 mg/kg every 3 weeks. In certain embodiments, treatment substantially increases invasive disease-free survival (IDFS) as compared to adjuvant treatment with trastuzumab. In certain embodiments, the treatment leads to a decrease in distant recurrence as compared to adjuvant treatment with trastuzumab. In certain embodiments, the adjuvant therapy provides a 50% reduction in the risk of invasive disease recurrence as compared to adjuvant therapy with trastuzumab. In certain embodiments, the adjuvant therapy provides a 40% reduction in the risk of distant recurrence as compared to adjuvant trastuzumab.

In another aspect, the present disclosure concerns a method for reducing the risk of cancer recurrence in a patient with HER2-positive early breast cancer comprising administering to the patient an effective amount of T-DM1, wherein the patient did not achieve pathologic complete response with neoadjuvant therapy and the patient had definitive surgery prior to the administering of T-DM1. In certain embodiments, the method does not comprise prior or concurrent adjuvant treatment with chemotherapy. In certain embodiments, the neoadjuvant therapy comprises a taxane and HER2 targeted therapy. In certain embodiments, the neoadjuvant therapy comprises a taxane and trastuzumab. In certain embodiments, the patient has completed at least 16 weeks of neoadjuvant therapy. In certain embodiments, the patient has completed at least 6 cycles of taxane-containing neoadjuvant therapy. In certain embodiments, the patient is subjected to treatment with T-DM1 no more than 12 weeks after definitive surgery. In certain embodiments, the definitive surgery is performed at least 14 days following the completion of neoadjuvant therapy. In certain embodiments, the definitive surgery is performed no later than 9 weeks following the completion of neoadjuvant therapy. In certain embodiments, the patient is subjected to treatment with an infusion of T-DM1 at a dose of 3.6 mg/kg every 3 weeks. In certain embodiments, the patient is subjected to treatment for fourteen cycles of an infusion of T-DM1 at a dose of 3.6 mg/kg every 3 weeks. In certain embodiments, the treatment substantially increases invasive disease-free survival (IDFS) as compared to adjuvant treatment with trastuzumab. In certain embodiments, the treatment leads to a decrease in distant recurrence as compared to adjuvant treatment with trastuzumab. In certain embodiments, the adjuvant therapy provides a 50% reduction in the risk of invasive disease recurrence as compared to adjuvant therapy with trastuzumab. In certain embodiments, the adjuvant therapy provides a 40% reduction in the risk of distant recurrence as compared to adjuvant trastuzumab.

BRIEF DESCRIPTION OF THE DRAWINGS

FIGS. 2A-2C depict summaries of the baseline characteristics of KATHERINE trial treatment arms.

FIG. 4B provides a summary of the site of first invasive-disease event in patients.

FIG. 5 provides a summary of secondary efficacy end points from the KATHERINE trial.

FIG. 7 provides a summary of the risk of first invasive-disease event by neoadjuvant HER2 targeted therapy in the intention-to-treat population

DETAILED DESCRIPTION

Figure 1:
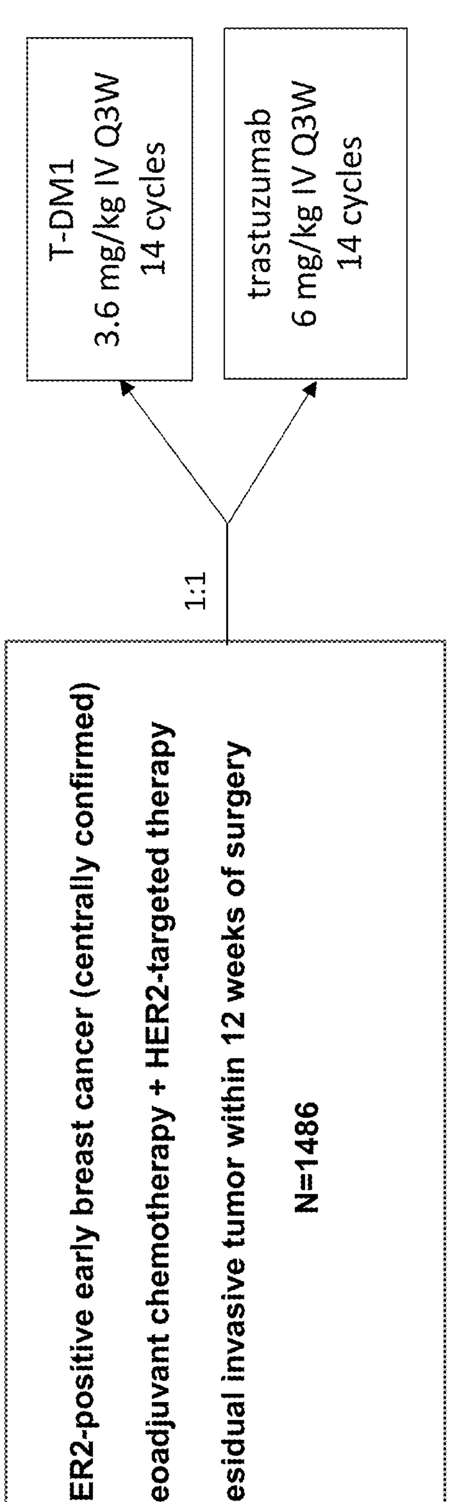
FIG. 1 is a schematic of the KATHERINE study design.

Reference will now be made in detail to certain embodiments of the present disclosure, examples of which are illustrated in the accompanying structures and formulas. While the present disclosure will be described in conjunction with the enumerated embodiments, it will be understood that they are not intended to limit the present disclosure to those embodiments. On the contrary, the present disclosure is intended to cover all alternatives, modifications, and equivalents which can be included within the scope of the present disclosure as defined by the claims. One skilled in the art will recognize many methods and materials similar or equivalent to those described herein, which could be used in the practice of the present disclosure. The present disclosure is in no way limited to the methods and materials described.

All references cited throughout the disclosure are expressly incorporated by reference herein in their entirety. In the event that one or more of the incorporated literature, patents, and similar materials differs from or contradicts this application, including but not limited to defined terms, term usage, described techniques, or the like, this application controls.

For purposes of clarity of disclosure and not by way of limitation, the detailed description is divided into the following subsections:

I. Definitions;
II. Trastuzumab emtansine;
III. Formulations of trastuzumab emtansine;
IV. Administration of trastuzumab emtansine;
V. Articles of Manufacture; and
VI. Exemplary Embodiments.

I. DEFINITIONS

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The terms "treat" and "treatment" refer to both therapeutic treatment and prophylactic or preventative measures, wherein the object is to prevent or slow down (lessen) an undesired physiological change or disorder, such as the growth, development or spread of a hyperproliferative condition, such as cancer. For purposes of the present disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "early stage breast cancer (EBC)" or "early breast cancer" is used herein to refer to breast cancer that has not spread beyond the breast or the axillary lymph nodes. This includes in situ and stage I, stage IIA, stage IIB, and stage IIIA breast cancers as well as breast cancers that have progressed beyond stage IIIA but have not progressed to stage IV.

Reference to a tumor or cancer as a "Stage 0," "Stage I," "Stage II," "Stage III," or "Stage IV", and various sub-stages within this classification, indicates classification of the tumor or cancer using the Overall Stage Grouping or Roman Numeral Staging methods known in the art. Although the actual stage of the cancer is dependent on the type of cancer, in general, a Stage 0 cancer is an in situ lesion, a Stage I cancer is small localized tumor, a Stage II and III cancer is a local advanced tumor which exhibits involvement of the local lymph nodes, and a Stage IV cancer represents metastatic cancer. The specific stages for each type of tumor is known to the skilled clinician.

The term "metastatic breast cancer" means the state of breast cancer where the cancer cells are transmitted from the original site to one or more sites elsewhere in the body, by the blood vessels or lymphatics, to form one or more secondary tumors in one or more organs besides the breast.

An "advanced" cancer is one which has spread outside the site or organ of origin, either by local invasion or metastasis. Accordingly, the term "advanced" cancer includes both locally advanced and metastatic disease.

A "refractory" cancer is one which progresses even though an anti-tumor agent, such as a chemotherapy, is being administered to the cancer patient. An example of a refractory cancer is one which is platinum refractory.

A "recurrent" cancer is one which has regrown, either at the initial site or at a distant site, after a response to initial therapy, such as surgery.

A "locally recurrent" cancer is cancer that returns after treatment in the same place as a previously treated cancer.

An "operable" or "resectable" cancer is cancer which is confined to the primary organ and suitable for surgery (resection).

A "non-resectable" or "unresectable" cancer, as used herein, is a cancer that is not able to be removed (resected) by surgery.

A "HER2-positive" cancer comprises cancer cells which have higher than normal levels of HER2. Examples of HER2-positive cancer include HER2-positive breast cancer and HER2-positive gastric cancer. Optionally, HER2-positive cancer has an immunohistochemistry (IHC) score of 2+ or 3+ and/or an in situ hybridization (ISH) amplification ratio≥2.0.

Herein, a "patient" or "subject" is a human patient. The patient can be a "cancer patient," i.e., one who is suffering or at risk for suffering from one or more symptoms of cancer, in particular gastric or breast cancer.

A "patient population," as used herein, refers to a group of cancer patients. Such populations can be used to demonstrate statistically significant efficacy and/or safety of a drug, such as Kadcyla.

A "relapsed" patient, as used herein, is one who has signs or symptoms of cancer after remission. Optionally, the patient has relapsed after adjuvant or neoadjuvant therapy.

A patient with "residual disease" is one did not achieve a pathological complete response (PCR) to a therapy. In certain embodiments, the residual disease is a pathological residual invasive disease in the breast and/or axillary node.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

"Neoadjuvant therapy" or "pre-operative therapy" or "pre-operative systemic treatment," as used herein, refers to therapy given prior to surgery. The goal of neoadjuvant therapy is to provide immediate systemic treatment, potentially eradicating micrometastases that would otherwise proliferate if the standard sequence of surgery followed by systemic therapy were followed. Neoadjuvant therapy can also help to reduce tumor size thereby allowing complete resection of initially unresectable tumors or preserving portions of the organ and its functions. Furthermore, neoadjuvant therapy permits an in vivo assessment of drug efficacy, which can guide the choice of subsequent treatments.

"Adjuvant therapy," as used herein, refers to therapy given after definitive surgery, so as to reduce the risk of disease recurrence. The goal of adjuvant therapy is to prevent recurrence of the cancer, and therefore to reduce the chance of cancer-related death. Adjuvant therapy herein specifically excludes neoadjuvant therapy.

"Definitive surgery" is used as that term is used within the medical community. Definitive surgery includes, for example, procedures, surgical or otherwise, that result in removal or resection of the tumor, including those that result in the removal or resection of all grossly visible tumor. Definitive surgery includes, for example, complete or curative resection or complete gross resection of the tumor. Definitive surgery includes procedures that occur in one or more stages, and includes, for example, multi-stage surgical procedures where one or more surgical or other procedures are performed prior to resection of the tumor. Definitive surgery includes procedures to remove or resect the tumor including involved organs, parts of organs and tissues, as well as surrounding organs, such as lymph nodes, parts of organs, or tissues. Removal can be incomplete such that tumor cells might remain even though undetected.

"Survival" refers to the patient remaining alive, and includes disease free survival (DFS), progression free survival (PFS) and overall survival (OS). Survival can be estimated by the Kaplan-Meier method, and any differences in survival are computed using the stratified log-rank test.

"Progression-Free Survival" (PFS) is the time from the first day of treatment to documented disease progression (including isolated CNS progression) or death from any cause on study, whichever occurs first.

"Disease free survival (DFS)" refers to the patient remaining alive, without return of the cancer, for a defined period of time such as about 1 year, about 2 years, about 3 years, about 4 years, about 5 years, about 10 years, etc., from initiation of treatment or from initial diagnosis. In one aspect of the present disclosure, DFS is analyzed according to the intent-to-treat principle, i.e., patients are evaluated on the basis of their assigned therapy. The events used in the analysis of DFS can include local, regional and distant recurrence of cancer, occurrence of secondary cancer, and death from any cause in patients without a prior event (e.g., breast cancer recurrence or second primary cancer).

"Invasive Disease Free Survival" (IDFS) refers to the time from patient randomization until the date of the first occurrence of an invasive-disease event, such as a recurrence of ipsilateral invasive breast tumor, recurrence of ipsilateral locoregional invasive disease, a distant disease recurrence, contralateral invasive breast cancer, or death from any cause "Overall survival," as used herein, refers to the patient remaining alive for a defined period of time, such as about 1 year, about 2 years, about 3 years, about 4 years, about 5 years, about 10 years, etc., from initiation of treatment or from initial diagnosis. In the studies underlying the present disclosure the event used for survival analysis was death from any cause.

"Extending survival," as used herein, refers to increasing DFS and/or OS in a treated patient relative to an untreated patient, or relative to a control treatment protocol. Survival is monitored for at least about six months, or at least about 1 year, or at least about 2 years, or at least about 3 years, or at least about 4 years, or at least about 5 years, or at least about 10 years, etc., following the initiation of treatment or following the initial diagnosis.

"Hazard ratio" in survival analysis is a summary of the difference between two survival curves, representing the reduction in the risk of death on treatment compared to control, over a period of follow-up. Hazard ratio is a statistical definition for rates of events. For the purpose of the present disclosure, hazard ratio is defined as representing the probability of an event in the experimental arm divided by the probability of an event in the control arm at any specific point in time.

"Monotherapy," as used herein, refers to a therapeutic regimen that includes only a single therapeutic agent for the treatment of the cancer or tumor during the course of the treatment period.

"Maintenance therapy," as used herein, refers to a therapeutic regimen that is given to reduce the likelihood of disease recurrence or progression. Maintenance therapy can be provided for any length of time, including extended time periods up to the life-span of the subject. Maintenance therapy can be provided after initial therapy or in conjunction with initial or additional therapies. Dosages used for maintenance therapy can vary and can include diminished dosages as compared to dosages used for other types of therapy.

As defined herein, the terms "trastuzumab," "HERCEPTIN®" and "huMAb4D5-8" are used interchangeably.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within Domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g., any one or more residues in the region from about residue 529 to about residue 625, inclusive, of HER2).

As defined herein, the terms "T-DM1," "trastuzumab-MCC-DM1," "ado-trastuzumab emtansine," "trastuzumab emtansine," and "KADCYLA®" are used interchangeably, and refer to trastuzumab linked through the linker moiety MCC to the maytansinoid drug moiety DM1, including all mixtures of variously loaded and attached antibody-drug conjugates where 1, 2, 3, 4, 5, 6, 7, and 8 drug moieties are covalently attached to the antibody trastuzumab (see U.S. Pat. No. 7,097,840; US 2005/0276812; US 2005/0166993, which are incorporated by reference herein in their entireties). Trastuzumab-MCC-DM1 contains an average of 3.5 DM1 molecules/antibody.

A "chemotherapy" is use of a chemotherapeutic agent useful in the treatment of cancer.

A "HER2 targeted therapy" or "HER2 directed therapy" are used interchangeably herein and refer to use of an agent that targets the HER2 pathway. Non-limiting examples of agents that target the HER2 pathway include trastuzumab, pertuzumab, lapatinib, neratinib, dacomitinib and afatinib.

Pertuzumab (also known as recombinant humanized monoclonal antibody 2C4, rhuMAb 2C4, PERJETA®, Genentech, Inc, South San Francisco) is another antibody treatment targeting Her2. Pertuzumab is a Her dimerization inhibitor (HDI) and functions to inhibit the ability of Her2 to form active heterodimers or homodimers with other Her receptors (such as EGFR/Her 1, Her2, Her3 and Her4). See, for example, Harari and Yarden Oncogene 19:6102-14 (2000); Yarden and Sliwkowski. Nat Rev Mol Cell Biol 2:127-37 (2001); Sliwkowski, Nat Struct Biol 10:158-9 (2003); Cho et al. Nature 421:756-60 (2003); and Malik et al., Pro Am Soc Cancer Res 44:176-7 (2003); U.S. Pat. No. 7,560,111.

Lapatinib, neratinib, dacomitinib, and afatinib are small molecule HER2 kinase inhibitors. Lapatinib (CAS 231277-92-2), used in the form of lapatinib ditosylate (Tyverb/Tykerb®) inhibits tyrosine kinase activity HER2/neu and EGFR (epidermal growth factor receptor). Further dual inhibitors of HER2/neu and EGFR are neratinib (CAS 698387-09-6, Nerlynx®) and afatinib (CAS 850140-72-6, Gilotrif®), whereas dacomitinib (CAS 1110813-31-4, Vizimpro®) is an inhibitor of EGFR, HER2 and HER4 tyrosine kinases, i.e. a pan-HER inhibitor.

The term "effective amount" refers to an amount of a drug effective to treat cancer in the patient. The effective amount of the drug can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug can prevent growth and/or kill existing cancer cells, it can be cytostatic and/or cytotoxic. The effective amount can extend progression free survival (e.g., as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g., as assessed by FOSI). The term "effective amount" specifically includes an amount suitable for achieving any of the primary or secondary endpoints of the clinical trial described in Example 1.

A "taxane" is a chemotherapy which inhibits mitosis and interferes with microtubules. Examples of taxanes include paclitaxel (TAXOL®; Bristol-Myers Squibb Oncology, Princeton, N.J.); cremophor-free, albumin-engineered nanoparticle formulation of paclitaxel or nab-paclitaxel (ABRAXANE™; American Pharmaceutical Partners, Schaumberg, Illinois); and docetaxel (TAXOTERE®; Rhône-Poulenc Rorer, Antony, France). A "taxane-based" or "taxane-containing" therapy is used interchangeably herein and refers to a therapy that includes a taxane.

"Chemotherapy-resistant" cancer, as used herein, means that the cancer patient has progressed while receiving a chemotherapy regimen (i.e., the patient is "chemotherapy refractory"), or the patient has progressed within 12 months (for instance, within 6 months) after completing a chemotherapy regimen.

A "fixed" or "flat" dose of a therapeutic agent, as used herein, refers to a dose that is administered to a human patient without regard for the weight (WT) or body surface area (BSA) of the patient. The fixed or flat dose is therefore not provided as a mg/kg dose or a mg/$m^2$ dose, but rather as an absolute amount of the therapeutic agent.

A "loading" dose, as used herein, generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose, as used herein, refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks, preferably every 3 weeks.

"Infusion" or "infusing," as used herein, refers to the introduction of a drug-containing solution into the body through a vein for therapeutic purposes. Generally, this is achieved via an intravenous (IV) bag.

An "intravenous bag" or "IV bag," as used herein, is a bag that can hold a solution which can be administered via the vein of a patient. In certain embodiments, the solution is a saline solution (e.g. about 0.9% or about 0.45% NaCl). Optionally, the IV bag is formed from polyolefin or polyvinyl chloride.

"Co-administering" or "co-administration," as used herein, refers to the intravenous administration of two (or more) drugs during the same administration, rather than sequential infusions of the two or more drugs. Generally, this will involve combining the two (or more) drugs into the same IV bag prior to co-administration thereof.

A drug that is administered "concurrently" with one or more other drugs is one that is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

A "vial" is a container suitable for holding a liquid or lyophilized preparation. In certain embodiments, the vial is a single-use vial, e.g. a 20-cc single-use vial with a stopper.

The term "package insert" is used to refer to instructions customarily included in commercial packages of therapeutic products, that contain information about the indications, usage, dosage, administration, contraindications and/or warnings concerning the use of such therapeutic products.

An "adverse event" is any unfavorable and unintended sign, symptom, or disease temporally associated with the use of an investigational (medicinal) product or other protocol-imposed intervention, regardless of attribution; and includes: AEs not previously observed in the patient that emerge during the protocol-specified AE reporting period, including signs or symptoms associated with breast cancer that were not present before the AE reporting period; complications that occur as a result of protocol-mandated interventions (e.g., invasive procedures such as biopsies); if applicable, AEs that occur before assignment of study treatment associated with medication washout, no treatment run-in, or other protocol-mandated intervention; Preexisting medical conditions (other than the condition being studied) judged by the investigator to have worsened in severity or frequency or changed in character during the protocol-specified AE reporting period An adverse event is classified as a "Serious Adverse Event" (SAE) if it meets the following criteria: results in death (i.e., the AE actually causes or leads to death); life threatening (i.e., the AE, in the view of the investigator, places the patient at immediate risk of death, but not including an AE that, had it occurred in a more severe form, might have caused death); requires or prolongs inpatient hospitalization; results in persistent or significant disability/incapacity (i.e., the AE results in substantial disruption of the patient's ability to conduct normal life functions); results in a congenital anomaly/birth defect in a neonate/infant born to a mother exposed to the investigational product; or is considered a significant medical event by the investigator based on medical judgment (e.g., can jeopardize the patient or can require medical/surgical intervention to prevent one of the outcomes listed above). All AEs that do not meet any of the criteria for serious are regarded as non-serious AEs. The terms "severe" and "serious" are not synonymous. Severity (or intensity) refers to the grade of a specific AE, e.g., mild (Grade 1), moderate (Grade 2), or severe (Grade 3) myocardial infarction. "Serious" is a regulatory definition (see previous definition) and is based on patient or event outcome or action criteria usually associated with events that pose a threat to a patient's life or functioning. Seriousness (not severity) serves as the guide for defining regulatory reporting obligations from the Sponsor to applicable regulatory authorities. Severity and seriousness should be independently assessed when recording AEs and SAEs on the eCRF

II. TRASTUZUMAB EMTANSINE

The present disclosure includes therapeutic treatments with trastuzumab emtansine (T-DM1), an antibody-drug conjugate (CAS Reg. No. 139504-50-0, trastuzumab-MCC-DM1, $N^{2'}$-(3-{1-[4-(trastuzumab)-1/3.5 carbamoylcyclohexylmethy]-2,5-dioxo-pyrrolidin-3-ylsulfanyl}-propionyl)-deacetylmaytansine), which has the structure:

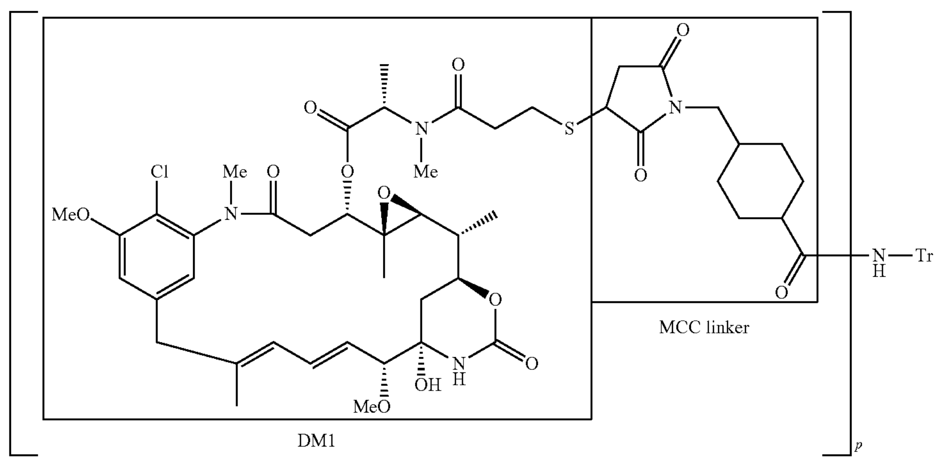

wherein Tr is trastuzumab linked through linker moiety MCC to the maytansinoid drug moiety DM1 (U.S. Pat. Nos. 5,208,020; 6,441,163). The microtubule inhibitory drug maytansinoid DM1 is synthesized from the maytansinoid maytansinol and is primarily linked to antibody lysine residues using the heterobifunctional reagent, SMCC. The drug to antibody ratio or drug loading is represented by p in the above structure of trastuzumab emtansine (Trastuzumab-MCC-DM1), and ranges in integer values from 1 to about 8. Trastuzumab-MCC-DM1 includes all mixtures of variously loaded and attached antibody-drug conjugates where 1, 2, 3, 4, 5, 6, 7, and 8 drug moieties are covalently attached to the antibody trastuzumab (U.S. Pat. No. 7,097,840; US 2005/0276812; US 2005/0166993). On average, trastuzumab emtansine contains 3.5 DM1 molecules/antibody.

Trastuzumab can be produced by a mammalian cell (Chinese Hamster Ovary, CHO) suspension culture. The HER2 (or c-erbB2) proto-oncogene encodes a transmembrane receptor protein of 185 kDa, which is structurally related to the epidermal growth factor receptor. Trastuzumab is an anti-HER2 antibody that has antigen binding residues of, or derived from, the murine 4D5 antibody (ATCC CRL 10463, deposited with American Type Culture Collection, 12301 Parklawn Drive, Rockville, Md. 20852 under the Budapest Treaty on Can 24, 1990). Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as in U.S. Pat. No. 5,821,337.

Trastuzumab emtansine can be prepared according to Example 1 of U.S. Application Publication No. 20110165155, for example, which is incorporated by reference herein in its entirety.

III. FORMULATIONS OF TRASTUZUMAB EMTANSINE

Trastuzumab emtansine (ado-trastuzumab emtansine, T-DM1) can be formulated in accordance with standard pharmaceutical practice. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present disclosure is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present disclosure or pharmaceutical composition thereof) or aid in the manufacturing of the pharmaceutical product (i.e., medicament).

The formulations can be prepared using conventional dissolution and mixing procedures. For example, the bulk drug substance (i.e., compound of the present disclosure or stabilized form of the compound (e.g., complex with a cyclodextrin derivative or other known complexation agent) is dissolved in a suitable solvent in the presence of one or more of the excipients described above. The compound of the present disclosure is typically formulated into pharmaceutical dosage forms to provide an easily controllable dosage of the drug and to enable patient compliance with the prescribed regimen.

The pharmaceutical composition (or formulation) for application can be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical formulations can be prepared for various routes and types of administration with pharmaceutically acceptable diluents, carriers, excipients or stabilizers (Remington's Pharmaceutical Sciences (1995) 18th edition, Mack Publ. Co., Easton, PA), in the form of a lyophilized formulation, milled powder, or an aqueous solution. Formulation can be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but can range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations of the present disclosure will be dosed and administered in a fashion, i.e., amounts, concentrations, schedules, course, vehicles and route of administration, consistent with good medical practice. Factors for consideration in this context include the particular disorder being treated, the clinical condition of the individual patient, the cause of the disorder, the site of delivery of the agent, the method of administration, the scheduling of administration, and other factors known to medical practitioners.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl, ethanol, or benzylalcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, including Tween 80, PLURONICS™ or polyethylene glycol (PEG), including PEG400. The active pharmaceutical ingredients can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, PA. Other examples of drug formulations can be found in Liberman, H. A. and Lachman, L., Eds., Pharmaceutical Dosage Forms, Marcel Decker, Vol 3, $2^{nd}$ Ed., New York, NY.

The pharmaceutical formulations include those suitable for the administration routes detailed herein. The formulations can conveniently be presented in unit dosage form and can be prepared by any of the methods well known in the art of pharmacy. Techniques and formulations generally are found in Remington's Pharmaceutical Sciences $18^{th}$ Ed. (1995) Mack Publishing Co., Easton, PA. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Pharmaceutical compositions can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can be a solution or a suspension in a non-toxic parenterally acceptable diluent or solvent, such as a solution in 1,3-butanediol or prepared from a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight per weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

As a general proposition, the initial pharmaceutically effective amount of T-DM1 administered per dose will be in the range of about 0.3 to 15 mg/kg/day of patient body weight.

A commercial T-DM1 formulation (KADCYLA®, trastuzumab emtansine) is a sterile, white to off-white preservative free lyophilized powder in single-use vials. Each vial contains 100 mg or 160 mg trastuzumab emtansine. Following reconstitution, each single-use vial contains trastuzumab emtansine (20 mg/mL), polysorbate 20 [0.02% (w/v)], sodium succinate (10 mM), and sucrose [6% (w/v)] with a pH of 5.0 and density of 1.026 g/mL. The resulting solution containing 20 mg/mL trastuzumab emtansine is administered by intravenous infusion following dilution.

IV. ADMINISTRATION OF TRASTUZUMAB EMTANSINE

The present disclosure is directed to the use of trastuzumab emtansine (T-DM1) as an adjuvant therapy. In certain embodiments, T-DM1 is used as an adjuvant therapy for treating a HER2-positive early breast cancer in a patient, e.g., in an adult patient. In certain embodiments, T-DM1 is used as an adjuvant therapy for treating a patient with HER2-positive, non-metastatic, invasive breast cancer. In certain embodiments, T-DM1 can be administered as a monotherapy, e.g., in individuals that have residual disease following a pre-operative systemic treatment.

In certain embodiments, the adjuvant therapy methods and uses of the present disclosure substantially increase invasive disease-free survival (IDFS) as compared to adjuvant therapy with trastuzumab. In certain embodiments, the adjuvant therapy provides a reduction in the risk of invasive disease recurrence of about 40%, of about 50% or of about 60% as compared to adjuvant therapy with trastuzumab. For example, but not by way of limitation, the adjuvant therapy disclosed herein provides a 50% reduction in the risk of invasive disease recurrence as compared to adjuvant therapy with trastuzumab. In certain embodiments, the adjuvant therapy leads to a decrease in distant recurrence as compared to adjuvant therapy with trastuzumab. For example, but not by way of limitation, the adjuvant therapy provides a 40% reduction in the risk of distant recurrence as compared to adjuvant trastuzumab.

The present disclosure provides methods for adjuvant therapy that includes administering T-DM1. For example, but not by way of limitation, the methods of adjuvant therapy include administering to a patient with HER2-positive early breast cancer an effective amount of T-DM1 as a monotherapy, where the patient has residual disease after a pre-operative systemic treatment.

In certain embodiments, the residual disease is in the breast and/or lymph node. For example, but not by way of limitation, the residual disease is in the breast. Alternatively and/or additionally, the residual disease is in a lymph node, e.g., an axillary lymph node. In certain embodiments, the residual disease is in the breast and in the lymph node.

In certain embodiments, the pre-operative systemic treatment includes a HER2 targeted therapy, e.g., one or more HER2 targeted therapies. Non-limiting examples of a HER2 targeted therapy includes trastuzumab, pertuzumab, lapatinib, neratinib, dacomitinib and/or afatinib. In certain embodiments, the HER2 targeted therapy is trastuzumab. In certain embodiments, the HER2 targeted therapy is pertuzumab. In certain embodiments, the HER2 targeted therapy is lapatinib. In certain embodiments, the HER2 targeted therapy is neratinib. In certain embodiments, the HER2 targeted therapy is dacomitinib. In certain embodiments, the HER2 targeted therapy is afatinib.

In certain embodiments, the pre-operative systemic treatment can include the administration of a taxane. Non-limiting examples of taxanes include paclitaxel and docetaxel. In certain embodiments, the taxane is paclitaxel. In certain embodiments, the taxane is docetaxel.

In certain embodiments, the method can include administration of a taxane-containing chemotherapy regimen and a HER2 targeted therapy. For example, but not by way of limitation, the patient has completed at least 16 weeks of pre-operative systemic treatment with a taxane-containing chemotherapy regimen and HER2 targeted therapy, e.g., prior to treatment with T-DM1. In certain embodiments, the patient has completed at least 6 cycles of a taxane-containing chemotherapy.

In certain embodiments, the methods of the present disclosure can further include definitive surgery. For example, but not by way of limitation, the patient is subjected to definitive surgery prior to the administration of T-DM1. In certain embodiments, the patient is administered T-DM1 no more than 1 week, no more than 2 weeks, no more than 3 weeks, no more than 4 weeks, no more than 5 weeks, no more than 6 weeks, no more than 7 weeks, no more than 8 weeks, no more than 9 weeks, no more than 10 weeks, no more than 11 weeks or no more than 12 weeks after the definitive surgery. In certain embodiments, the patient is administered T-DM1 no more than 12 weeks after the definitive surgery.

The presently disclosed subject matter further provides methods for the treatment of breast cancer in a patient with HER2-positive early breast cancer who has residual disease in the breast or axillary lymph nodes after neoadjuvant therapy with chemotherapy and a HER2 targeted therapy. In certain embodiments, the method can include removing all clinically evident tumor cells in the breast and axillary lymph nodes by definitive surgery and subjecting the patient to monotherapy adjuvant therapy with T-DM1.

In certain embodiments, the patient has residual disease in the breast or axillary lymph nodes after neoadjuvant therapy with a taxane and a HER2 targeted therapy. In certain embodiments, the patient has completed at least 16 weeks of neoadjuvant therapy with a taxane-containing chemotherapy. In certain embodiments, the patient has completed at least 6 cycles of taxane-containing chemotherapy. In certain embodiments, the patient is subjected to adjuvant treatment with T-DM1 no more than 12 weeks after definitive surgery.

The presently disclosed subject matter further provides methods for treating HER2-positive early breast cancer in a patient with residual disease following neoadjuvant therapy. In certain embodiments, the method includes administering to the patient an effective amount of T-DM1 after the patient is subjected to definitive surgery. In certain embodiments, the residual disease is a pathological residual invasive disease. In certain embodiments, the residual disease is a pathological residual invasive disease in a lymph node. In certain embodiments, the residual disease is a pathological residual invasive disease in a breast. In certain embodiments, the residual disease is a pathological residual invasive disease in a lymph node and in a breast.

The presently disclosed subject matter provides methods for reducing the risk of cancer recurrence in a patient with HER2-positive early breast cancer. In certain embodiments, the method includes administering to the patient an effective amount of T-DM1, where the patient did not achieve pathologic complete response with neoadjuvant therapy and the patient had definitive surgery prior to the administering of T-DM1.

In certain embodiments, the neoadjuvant therapy includes a taxane and/or HER2 targeted therapy. In certain embodiments, the neoadjuvant therapy includes a taxane and HER2 targeted therapy. For example, but not by way of limitation, the neoadjuvant therapy includes a taxane and trastuzumab. In certain embodiments, a patient being treated according to the methods of the present disclosure has completed at least 16 weeks of neoadjuvant therapy. In certain embodiments, the patient has completed at least 6 cycles of taxane-containing neoadjuvant therapy. In certain embodiments, the patient is subjected to treatment with T-DM1 no more than 12 weeks after definitive surgery.

In certain embodiments, the methods of the present disclosure do not include prior or concurrent adjuvant treatment with chemotherapy.

In certain embodiments, the methods of the present disclosure can include the administration of T-DM1 at a dose of 3.6 mg/kg every 3 weeks. For example, but not by way of limitation, the patient can be administered T-DM1 for fourteen cycles at a dose of 3.6 mg/kg every 3 weeks.

The present disclosure further provides trastuzumab emtansine (T-DM1), and pharmaceutical compositions thereof, for use as an adjuvant therapy for HER2-positive early breast cancer in a patient. In certain embodiments, T-DM1 is administered a monotherapy and the patient has residual disease after a pre-operative systemic treatment. In certain embodiments, the residual disease is present in a breast, present in a lymph node, or present in a breast and a lymph node. In certain embodiments, the pre-operative systemic treatment includes a HER2 targeted therapy, e.g., trastuzumab or trastuzumab and pertuzumab, lapatinib, neratinib, dacomitinib and/or afatinib. In certain embodiments, the pre-operative systemic treatment further comprises a taxane. In certain embodiments, the patient is subjected to a definitive surgery prior to the administration of T-DM1.

In a further aspect, the presently disclosed subject matter provides the use of T-DM1 in the manufacture of a medicament for use in an adjuvant therapy for HER2-positive early breast cancer in a patient, where the adjuvant is a monotherapy and wherein the patient has residual disease after a pre-operative systemic treatment. In certain embodiments, the residual disease is present in a breast, present in a lymph node, or present in a breast and a lymph node. In certain embodiments, the pre-operative systemic treatment includes a HER2 targeted therapy, e.g., trastuzumab or trastuzumab and pertuzumab, lapatinib, neratinib, dacomitinib and/or afatinib. In certain embodiments, the pre-operative systemic treatment further comprises a taxane. In certain embodiments, the patient is subjected to a definitive surgery prior to the administration of T-DM1.

Trastuzumab emtansine (T-DM1), and pharmaceutical compositions thereof, can be administered by any route in the methods of the present disclosure and as appropriate to the condition to be treated. For example, but not by way of limitation, suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. For local immunosuppressive treatment, the compounds can be administered by intralesional administration, including perfusing or otherwise contacting the graft with the inhibitor before transplantation. It will be appreciated that the preferred route can vary with for example the condition of the recipient. Where the compound is administered orally, it can be formulated as a pill, capsule, tablet, etc. with a pharmaceutically acceptable carrier, glidant, or excipient. Where the compound is administered parenterally, it can be formulated with a pharmaceutically acceptable parenteral vehicle or diluent, and in a unit dosage injectable form, as detailed below.

V. ARTICLES OF MANUFACTURE

Articles of manufacture, or "kits," containing T-DM1 useful for the treatment methods herein are provided. In certain embodiments, the kit comprises a container comprising T-DM1. The kit can further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container can be formed from a variety of materials such as glass or plastic. The container can hold T-DM1 or a formulation thereof which is effective for use in a treatment method herein, and can have a sterile access port (for example, the container can be an intravenous solution bag or a vial having a stopper pierceable by a hypodermic injection needle). The label or package insert indicates that the composition is used in a treatment method as described and claimed herein. The article of manufacture can also contain a further container comprising a pharmaceutically acceptable buffer, such as bacteriostatic water for injection (BWFI), phosphate-buffered saline, Ringer's solution and dextrose solution. It can further include other materials desirable from a commercial and user standpoint, including other buffers, diluents, filters, needles, and syringes.

The kit can further comprise directions for the administration of T-DM1. For example, if the kit comprises a first composition comprising T-DM1 and a second pharmaceutical formulation, the kit can further comprise directions for the simultaneous, sequential or separate administration of the first and second pharmaceutical compositions to a patient in need thereof.

In certain embodiments, the kits are suitable for the delivery of solid oral forms of T-DM1, such as tablets or capsules. Such a kit preferably includes a number of unit dosages. Such kits can include a card having the dosages oriented in the order of their intended use. An example of such a kit is a "blister pack." Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

In certain embodiments, an article of manufacture herein comprises an intravenous (IV) bag containing a stable mixture of T-DM1 suitable for administration to a cancer patient. Optionally, the mixture is in saline solution; for example, comprising about 0.9% NaCl or about 0.45% NaCl. An exemplary IV bag is a polyolefin or polyvinyl chloride infusion bag, e.g., a 250 mL IV bag. According to certain embodiments of the present disclosure, the bag includes a from about 100 mg to about 160 mg T-DM1.

Optionally, the mixture in the IV bag is stable for up to 24 hours at 5° C. or 30° C. Stability of the mixture can be evaluated by one or more assays selected from the group consisting of: color, appearance and clarity (CAC), concentration and turbidity analysis, particulate analysis, size exclusion chromatography (SEC), ion-exchange chromatography (IEC), capillary zone electrophoresis (CZE), image capillary isoelectric focusing (iCIEF), and potency assay.

VI. EXEMPLARY EMBODIMENTS

A. In certain non-limiting embodiments, the presently disclosed subject matter provides for a method of adjuvant therapy comprising administering to a patient with HER2-positive early breast cancer an effective amount of trastuzumab emtansine (T-DM1) as a monotherapy, wherein the patient has residual disease after a pre-operative systemic treatment.

A1. The foregoing method of A, wherein the residual disease is present in a breast.

A2. The foregoing method of A, wherein the residual disease is present in a lymph node.

A3. The foregoing method of A, wherein the residual disease is present in a breast and a lymph node.

A4. The foregoing method of any one of A-A3, wherein the pre-operative systemic treatment comprises a HER2 targeted therapy.

A5. The foregoing method of A4, wherein the HER2 targeted therapy comprises trastuzumab.

A6. The foregoing method of A5, wherein the HER2 targeted therapy further comprises pertuzumab.

A7. The foregoing method of A4 or A5, wherein the HER2 targeted therapy further comprises an agent selected from the group consisting of lapatinib, neratinib, dacomitinib, afatinib and a combination thereof.

A8. The foregoing method of any one of A-A7, wherein the pre-operative systemic treatment further comprises a taxane.

A9. The foregoing method of any one of A-A8, wherein the patient is an adult patient.

A10. The foregoing method of any one of A-A9, wherein the patient is subjected to a definitive surgery prior to the administration of T-DM1.

A11. The foregoing method of A10, wherein the patient is administered T-DM1 no more than 12 weeks after the definitive surgery.

A12. The foregoing method of any one of A-A1, wherein the patient has completed at least 16 weeks of pre-operative systemic treatment with a taxane-containing chemotherapy regimen and HER2 targeted therapy.

A13. The foregoing method of any one of A-A12, wherein the patient has completed at least 6 cycles of taxane-containing chemotherapy.

A14. The foregoing method of any one of A-A13, wherein the patient is administered T-DM1 at a dose of 3.6 mg/kg every 3 weeks.

A15. The foregoing method of any one of A-A14, wherein the patient is administered T-DM1 for fourteen cycles at a dose of 3.6 mg/kg every 3 weeks.

A16. The foregoing method of any one of A-A15, wherein the adjuvant therapy substantially increases invasive disease-free survival (IDFS) as compared to adjuvant therapy with trastuzumab.

A17. The foregoing method of any one of A-A16, wherein the adjuvant therapy provides a 50% reduction in the risk of invasive disease recurrence as compared to adjuvant therapy with trastuzumab.

A18. The foregoing method of any one of A-A17, wherein the adjuvant therapy leads to a decrease in distant recurrence as compared to adjuvant therapy with trastuzumab.

A19. The foregoing method of any one of A-A18, wherein the adjuvant therapy provides a 40% reduction in the risk of distant recurrence as compared to adjuvant trastuzumab.

B. In certain embodiments, the presently disclosed subject matter provides trastuzumab emtansine (T-DM1) for use in an adjuvant therapy HER2-positive early breast cancer in a patient, wherein the adjuvant is a monotherapy and wherein the patient has residual disease after a pre-operative systemic treatment.

B1. The foregoing use of T-DM1 of B, wherein the residual disease is present in a breast, present in a lymph node, or present in a breast and a lymph node.

B2. The foregoing use of T-DM1 of B or B1, wherein the pre-operative systemic treatment comprises a HER2 targeted therapy.

B3. The foregoing use of T-DM1 of B2, wherein the HER2 targeted therapy comprises trastuzumab or trastuzumab and pertuzumab, lapatinib, neratinib, dacomitinib and/or afatinib.

B4. The foregoing use of T-DM1 of any one of B-B3, wherein the pre-operative systemic treatment further comprises a taxane.

B5. The foregoing use of T-DM1 of any one of B-B4, wherein the patient is an adult patient.

B6. The foregoing use of T-DM1 of any one of B-B5, wherein the patient is subjected to a definitive surgery prior to the administration of T-DM1.

B7. The foregoing use of T-DM1 of any one of B-B6, wherein the adjuvant therapy substantially increases invasive disease-free survival (IDFS) as compared to adjuvant therapy with trastuzumab.

B8. The foregoing use of T-DM1 of any one of B-B7, wherein the adjuvant therapy provides a 50% reduction in the risk of invasive disease recurrence as compared to adjuvant therapy with trastuzumab.

B9. The foregoing use of T-DM1 of any one of B-B8, wherein the adjuvant therapy leads to a decrease in distant recurrence as compared to adjuvant therapy with trastuzumab.

B10. The foregoing use of T-DM1 of any one of B-B9, wherein the adjuvant therapy provides a 40% reduction in the risk of distant recurrence as compared to adjuvant trastuzumab.

C. In certain embodiments, the presently disclosed subject matter provides the use of trastuzumab emtansine (T-DM1) in the manufacture of a medicament for use in an adjuvant therapy HER2-positive early breast cancer in a patient, wherein the adjuvant is a monotherapy and wherein the patient has residual disease after a pre-operative systemic treatment.

C1. The foregoing use of C, wherein the residual disease is present in a breast, present in a lymph node, or present in a breast and a lymph node.

C2. The foregoing use of C or C1, wherein the pre-operative systemic treatment comprises a HER2 targeted therapy.

C3. The foregoing use of C2, wherein the HER2 targeted therapy comprises trastuzumab or trastuzumab and pertuzumab, lapatinib, neratinib, dacomitinib and/or afatinib.

C4. The foregoing use of any one of C-C3, wherein the pre-operative systemic treatment further comprises a taxane.

C5. The foregoing use of any one of C-C4, wherein the patient is an adult patient.

C6. The foregoing use of any one of C-C5, wherein the patient is subjected to a definitive surgery prior to the administration of T-DM1.

C7. The foregoing use of any one of C-C6, wherein the adjuvant therapy substantially increases invasive disease-free survival (IDFS) as compared to adjuvant therapy with trastuzumab.

C8. The foregoing use of any one of C-C7, wherein the adjuvant therapy provides a 50% reduction in the risk of invasive disease recurrence as compared to adjuvant therapy with trastuzumab.

C9. The foregoing use of any one of C-C8, wherein the adjuvant therapy leads to a decrease in distant recurrence as compared to adjuvant therapy with trastuzumab.

C10. The foregoing use of any one of C-C9, wherein the adjuvant therapy provides a 40% reduction in the risk of distant recurrence as compared to adjuvant trastuzumab.

D. In certain non-limiting embodiments, the presently disclosed subject matter provides for a method for the treatment of breast cancer in a patient with HER2-positive early breast cancer who has residual disease in the breast or axillary lymph nodes after neoadjuvant therapy with chemotherapy and HER2 targeted therapy comprising:

(i) removing all clinically evident tumor cells in the breast and axillary lymph nodes by definitive surgery; and (ii) subjecting the patient to monotherapy adjuvant therapy with trastuzumab emtansine (T-DM1).

D1. The foregoing method of D, wherein the patient has residual disease in the breast or axillary lymph nodes after neoadjuvant therapy with a taxane and HER2 targeted therapy.

D2. The foregoing method of D or D1, wherein the patient has completed at least 16 weeks of neoadjuvant therapy with a taxane-containing chemotherapy.

D3. The foregoing method of any one of D-D2, wherein the patient has completed at least 6 cycles of taxane-containing chemotherapy.

D4. The foregoing method of any one of D-D3, wherein the patient is subjected to adjuvant treatment with T-DM1 no more than 12 weeks after definitive surgery.

D5. The foregoing method of any one of D-D4, wherein the patient is subjected to adjuvant treatment with an infusion of T-DM1 at a dose of 3.6 mg/kg every 3 weeks.

D6. The foregoing method of any one of D-D5, wherein the patient is subjected to adjuvant treatment for fourteen cycles of an infusion of T-DM1 at a dose of 3.6 mg/kg every 3 weeks.

D7. The foregoing method of any one of D-D6, wherein the treatment substantially increases invasive disease-free survival (IDFS) as compared to adjuvant treatment with trastuzumab.

D8. The foregoing method of any one of D-D7, wherein the treatment leads to a decrease in distant recurrence as compared to adjuvant treatment with trastuzumab.

E. In certain non-limiting embodiments, the presently disclosed subject matter provides for a method for the treatment of HER2-positive early breast cancer in a patient with residual disease following neoadjuvant therapy, the method comprising administering to the patient an effective amount of trastuzumab emtansine (T-DM1) after the patient is subjected to definitive surgery.

E1. The foregoing method of E, wherein the residual disease is a pathological residual invasive disease.

E2. The foregoing method of E or E1, wherein the residual disease is a pathological residual invasive disease in a lymph node.

E3. The foregoing method of any one of E-E2, wherein the residual disease is a pathological residual invasive disease in a breast.

E4. The foregoing method of any one of E-E3, wherein the method does not comprise prior or concurrent adjuvant treatment with chemotherapy.

E5. The foregoing method of any one of E-E4, wherein the neoadjuvant therapy comprises a taxane and HER2 targeted therapy.

E6. The foregoing method of any one of E-E5, wherein the neoadjuvant therapy comprises a taxane and trastuzumab.

E7. The foregoing method of any one of E-E6, wherein the patient has completed at least 16 weeks of neoadjuvant therapy.

E8. The foregoing method of any one of E-E7, wherein the patient has completed at least 6 cycles of taxane-containing neoadjuvant therapy.

E9. The foregoing method of any one of E-E8, wherein the patient is subjected to treatment with T-DM1 no more than 12 weeks after definitive surgery.

E10. The foregoing method of any one of E-E9, wherein the patient is subjected to treatment with an infusion of T-DM1 at a dose of 3.6 mg/kg every 3 weeks.

E11. The foregoing method of any one of E-E10, wherein the patient is subjected to treatment for fourteen cycles of an infusion of T-DM1 at a dose of 3.6 mg/kg every 3 weeks.

E12. The foregoing method of any one of E-E11, wherein the treatment substantially increases invasive disease-free survival (IDFS) as compared to adjuvant treatment with trastuzumab.

E13. The foregoing method of any one of E-E12, wherein the treatment leads to a decrease in distant recurrence as compared to adjuvant treatment with trastuzumab.

F. In certain non-limiting embodiments, the presently disclosed subject matter provides for a method for reducing the risk of cancer recurrence in a patient with HER2-positive early breast cancer comprising administering to the patient an effective amount of trastuzumab emtansine (T-DM1), wherein the patient did not achieve pathologic complete response with neoadjuvant therapy and the patient had definitive surgery prior to the administering of T-DM1.

F1. The foregoing method of F, wherein the method does not comprise prior or concurrent adjuvant treatment with chemotherapy.

F2. The foregoing method of F or F1, wherein the neoadjuvant therapy comprises a taxane and HER2 targeted therapy.

F3. The foregoing method of any one of F-F2, wherein the neoadjuvant therapy comprises a taxane-containing chemotherapy regimen and trastuzumab.

F4. The foregoing method of any one of F-F3, wherein the patient has completed at least 16 weeks of neoadjuvant therapy.

F5. The foregoing method of any one of F-F4, wherein the patient has completed at least 6 cycles of taxane-containing neoadjuvant therapy.

F6. The foregoing method of any one of F-F5, wherein the patient is subjected to treatment with T-DM1 no more than 12 weeks after definitive surgery.

F7. The foregoing method of any one of F-F6, wherein the patient is subjected to treatment with an infusion of T-DM1 at a dose of 3.6 mg/kg every 3 weeks.

F8. The foregoing method of any one of F-F7, wherein the patient is subjected to treatment for fourteen cycles of an infusion of T-DM1 at a dose of 3.6 mg/kg every 3 weeks.

F9. The foregoing method of any one of F-F8, wherein the treatment substantially increases invasive disease-free survival (IDFS) as compared to adjuvant treatment with trastuzumab.

F10. The foregoing method of any one of F-F9, wherein the treatment leads to a decrease in distant recurrence as compared to adjuvant treatment with trastuzumab.

F11. The foregoing method of any one of D-F10, wherein the adjuvant therapy provides a 50% reduction in the risk of invasive disease recurrence as compared to adjuvant therapy with trastuzumab.

F12. The foregoing method of any one of D-F11, wherein the adjuvant therapy provides a 40% reduction in the risk of distant recurrence as compared to adjuvant trastuzumab.

EXAMPLES

In order to illustrate the present disclosure, the following examples are included. However, it is to be understood that these examples do not limit the present disclosure and are only meant to suggest exemplary methods of practicing the present disclosure.

Example 1—Clinical Trial Design

Phase III Clinical Study

This phase 3, open-label study (NCT01772472/BO27938/NSABPB-50-I/GBG 77; KATHERINE) enrolled patients with HER2-positive early breast cancer who received neoadjuvant taxane-containing chemotherapy plus trastuzumab-containing HER2 targeted therapy and had pathologic residual invasive disease in the breast and/or axillary lymph nodes. Patients were randomized to adjuvant T-DM1 or trastuzumab for 14 cycles. The primary end point was invasive-disease-free survival (IDFS). The efficacy stopping boundary for this single prespecified interim analysis of IDFS was $P<0.0124$ or a hazard ratio of 0.732 or less.

Patients

The patient population for this study are patients with primary non-metastatic HER2-positive breast cancer.

Inclusion Criteria

Patients must meet the following criteria for study entry:

1. HER2-positive breast cancer. HER2-positive status will be based on pretreatment biopsy material and defined as an immunohistochemistry (IHC) score of 3+ and/or positive by in situ hybridization (ISH) prospectively confirmed by a central laboratory prior to study enrollment. ISH positivity is defined as a ratio of ≥2.0 for the number of HER2 gene copies to the number of signals for chromosome 17 copies. Formalin-fixed paraffin-embedded tumor tissue block or a partial block must be available for central evaluation of HER2 expression. If sites are unable to send a tissue block due to local regulations, at least 8 unstained slides should be sent for HER2 testing, and in addition up to 5 slides for exploratory biomarker research. A central laboratory will perform both IHC and ISH assays; however, only one positive result is required for eligibility. In the event that sufficient material from the pretreatment biopsy is not available for submission, central HER2 determination for eligibility can be performed on residual tumor tissue from the time of definitive surgery. Patients with synchronous bilateral invasive disease are eligible provided both lesions are HER2-positive.
2. Histologically confirmed invasive breast carcinoma.
3. Clinical stage at presentation: T1-4, N0-3, M0 (Note: Patients with T1a/bN0 tumors will not be eligible).
4. Completion of preoperative systemic chemotherapy and HER2 targeted treatment. Systemic therapy must consist of at least 6 cycles of chemotherapy, with a total duration at least 16 weeks, including at least 9 weeks of trastuzumab and at least 9 weeks of taxane-based chemotherapy. Patients can have received an anthracycline as part of preoperative therapy in addition to taxane chemotherapy. Patients receiving dose-dense chemotherapy regimens are eligible, provided at least 8 weeks of taxane-based therapy and at least 8 weeks of trastuzumab have been given. A dose-escalated (225 $mg/m^2$ q2w) dose-dense regimen of paclitaxel over 6 weeks is allowed. Patients can have received more than one HER2 targeted therapy. Note: HER2 targeted therapy alone periods will not satisfy the requirement for cycles of preoperative systemic chemotherapy. All systemic chemotherapy should be completed preoperatively.

5. Adequate excision: surgical removal of all clinically evident disease in the breast and lymph nodes as follows:

Breast surgery: total mastectomy with no gross residual disease at the margin of resection, or breast-conserving surgery with histologically negative margins of excision. For patients who undergo breast-conserving surgery, the margins of the resected specimen must be histologically free of invasive tumor and DCIS as determined by the local pathologist. If pathologic examination demonstrates tumor at the line of resection, additional operative procedures can be performed to obtain clear margins. If tumor is still present at the resected margin after re-excision(s), the patient must undergo total mastectomy to be eligible. Patients with margins positive for lobular carcinoma in situ (LCIS) are eligible without additional resection.

Lymph node surgery: In case of positive results from a fine-needle aspiration, core biopsy, or sentinel node biopsy performed prior to preoperative therapy, additional surgical evaluation of the axilla following preoperative therapy is required. If only micrometastases are present in sentinel nodes preoperatively (i.e., if the greatest diameter of the nodal metastasis in a sentinel node is 0.2 mm or less), no additional surgical evaluation of the axilla is required. If sentinel node biopsy performed before preoperative therapy was negative, no additional surgery evaluation of the axilla is required after preoperative therapy. If the only sentinel node identified by isotope scan is in the internal mammary chain, surgical evaluation of the axilla is recommended.

If sentinel node biopsy performed after preoperative therapy is positive, additional surgical evaluation of the axilla is recommended. If sentinel node evaluation after preoperative therapy is negative, no further additional surgical evaluation of the axilla is required. Axillary dissection without sentinel node evaluation is permitted after preoperative therapy.

6. Pathologic evidence of residual invasive carcinoma in the breast or axillary lymph nodes following completion of preoperative therapy. If invasive disease is present in both breasts, residual invasive carcinoma must be present in at least 1 breast or axillary lymph node postoperatively.
7. An interval of no more than 12 weeks between the date of primary surgery and the date of randomization.
8. Known hormone receptor status. Hormone receptor-positive status can be determined by either known positive ER or known positive PgR status; hormone receptor-negative status must be determined by both known negative ER and known negative PgR.
9. Signed written informed consent approved by the study site's Institutional Review Board (IRB)/Ethical Committee (EC).
10. Age≥18 years
11. Eastern Cooperative Oncology Group (ECOG) performance status 0 or 1
12. Life expectancy≥6 months
13. Adequate organ function during screening, defined as:

a. Absolute neutrophil count≥1200 cells/$mm^3$ b. Platelet count≥100000 cells/$mm^3$ c. Hemoglobin≥9.0 g/dL; patients can receive red blood cell transfusions to obtain this level d. Serum creatinine<1.5×upper limit of normal (ULN)

e. International normalized ratio (INR) and activated partial thromboplastin time (aPTT)≤1.5×ULN f. Serum AST and ALT≤1.5×ULN g. Serum total bilirubin (TBILI)≤1.0×ULN (within normal limits), except for patients with Gilbert's syndrome, for whom direct bilirubin should be within the normal range h. Serum alkaline phosphatase (ALK)≤1.5×ULN i. Screening LVEF≥50% on ECHO or MUGA after receiving neoadjuvant chemotherapy and no decrease in LVEF by more than 15% absolute points from the pre-chemotherapy LVEF. Or, if pre-chemotherapy LVEF was not assessed, the screening LVEF must be ≥55% after completion of neoadjuvant chemotherapy.

i. LVEF assessment can be repeated once up to 3 weeks following the initial screening assessment to assess eligibility.

14. For women who are not postmenopausal (≥12 months of non-therapy-induced amenorrhea) or surgically sterile (absence of ovaries and/or uterus): agreement to remain abstinent or use single or combined contraceptive methods that result in a failure rate of <1% per year during the treatment period and for at least 7 months after the last dose of study drug.

a. Abstinence is only acceptable if it is in line with the preferred and usual lifestyle of the patient. Periodic abstinence (e.g., calendar, ovulation, symptothermal, or postovulation methods) and withdrawal are not acceptable methods of contraception. Examples of contraceptive methods with a failure rate of <1% per year include tubal ligation, male sterilization, hormonal implants, established, proper use of combined oral or injected hormonal contraceptives, and certain intrauterine devices. Alternatively, two methods (e.g., two barrier methods such as a condom and a cervical cap) can be combined to achieve a failure rate of <1% per year. Barrier methods must always be supplemented with the use of a spermicide.

b. Male patients whose partners are pregnant must use condoms or truly refrain from sexual activity for the duration of the pregnancy.

15. Negative serum pregnancy test for premenopausal women including women who have had a tubal ligation and for women less than 12 months after the onset of menopause.
16. Documentation of hepatitis B virus (HBV) and hepatitis C virus (HCV) serologies is required: this includes HB surface antigen (HBsAg) and/or total HB core antibody (anti-HBc) in addition to HCV antibody testing. The most recent serologic testing must have occurred within 3 months prior to initiation of neoadjuvant therapy. If such testing has not been done, it must be performed during screening.

Exclusion Criteria

Patients who meet any of the following criteria are excluded from study entry:

Disease-Related Exclusion Criteria:

1. Stage IV (metastatic) breast cancer.
2. History of any prior (ipsi- or contralateral) breast cancer except lobular CIS
3. Evidence of clinically evident gross residual or recurrent disease following preoperative therapy and surgery.
4. An overall response of PD according to the investigator at the conclusion of preoperative systemic therapy.
5. Treatment with any anti-cancer investigational drug within 28 days prior to commencing study treatment.
6. History of other malignancy within the last 5 years except for appropriately treated CIS of the cervix, non-melanoma skin carcinoma, Stage I uterine cancer, or other non-breast malignancies with an outcome similar to those mentioned above.

7. Patients for whom radiotherapy would be recommended for breast cancer treatment but for whom it is contraindicated because of medical reasons (e.g., connective tissue disorder or prior ipsilateral breast radiation).
8. Current NCI CTCAE (Version 4.0) Grade≥2 peripheral neuropathy.
9. History of exposure to the following cumulative doses of anthracyclines:
   Doxorubicin>240 mg/$m^2$.
   Epirubicin or Liposomal Doxorubicin-Hydrochloride (Myocet®)>480 mg/$m^2$.
   For other anthracyclines, exposure equivalent to doxorubicin>240 mg/$m^2$.
10. Cardiopulmonary dysfunction as defined by any of the following:
   a. History of NCI CTCAE (Version 4.0) Grade≥3 symptomatic CHF or NYHA criteria Class≥II
   b. Angina pectoris requiring anti-anginal medication, serious cardiac arrhythmia not controlled by adequate medication, severe conduction abnormality, or clinically significant valvular disease.
   c. High-risk uncontrolled arrhythmias: i.e., atrial tachycardia with a heart rate>100/min at rest, significant ventricular arrhythmia (ventricular tachycardia) or higher-grade AV-block (second degree AV-block Type 2 [Mobitz 2] or third-degree AV-block).
   d. Significant symptoms (Grade≥2) relating to left ventricular dysfunction, cardiac arrhythmia, or cardiac ischemia while or since receiving preoperative therapy.
   e. History of a decrease in LVEF to <40% with prior trastuzumab treatment (e.g., during preoperative therapy).
   f. Uncontrolled hypertension (systolic blood pressure>180 mmHg and/or diastolic blood pressure>100 mmHg).
   g. Evidence of transmural infarction on ECG Requirement for continuous oxygen therapy.
11. Prior treatment with trastuzumab emtansine.

General Exclusion Criteria

12. Current severe, uncontrolled systemic disease (e.g., clinically significant cardiovascular, pulmonary, or metabolic disease; wound-healing disorders; ulcers).
13. For female patients, current pregnancy and/or lactation.
14. Major surgical procedure unrelated to breast cancer or significant traumatic injury within approximately 28 days prior to randomization or anticipation of the need for major surgery during the course of study treatment.
15. Any known active liver disease, for example, disease due to HBV, HCV, autoimmune hepatic disorders, or sclerosing cholangitis. Patients who have positive HBV or HCV serologies without known active disease must meet the eligibility criteria for ALT, AST, TBILI, INR, aPTT, and alkaline phosphatase (ALK) on at least two consecutive occasions, separated by at least 1 week, within the 30 day screening period.
16. Concurrent, serious, uncontrolled infections or known infection with HI.
17. History of intolerance, including Grade 3 to 4 infusion reaction or hypersensitivity to trastuzumab or murine proteins or any components of the product.
18. Active, unresolved infections at screening requiring treatment.
19. Assessment by the investigator as being unable or unwilling to comply with the requirements of the protocol.

Study Design

Patients who have consented and are eligible for the study will be randomized to one of the following treatment arms in a 1:1 ratio:

Arm A: Trastuzumab emtansine 3.6 mg/kg given IV q3w for 14 cycles.

Arm B: Trastuzumab 6 mg/kg given IV q3w for 14 cycles (an 8 mg/kg loading dose should be given in cases where there has been an interval greater than 6 weeks since the last dose of trastuzumab).

The study will enroll approximately 1484 patients who have pathologically documented residual invasive disease in either the breast or axillary lymph nodes following completion of preoperative therapy. Patients must have completed preoperative systemic treatment consisting of at least 6 cycles with a total duration of at least 16 weeks, including at least 9 weeks of trastuzumab and at least 9 weeks of taxane-based chemotherapy (or, if receiving dose-dense chemotherapy regimens, at least 6-8 weeks of taxane-based therapy and at least 8 weeks of trastuzumab).

HER2 targeted therapy and chemotherapy can be given concurrently; patients can have received more than one HER2 targeted therapy. Patients can have received an anthracycline as part of preoperative therapy.

Patients will receive study treatment for a maximum of 14 cycles; treatment will be discontinued prior to 14 cycles in the event of disease recurrence, unacceptable toxicity, or study termination by the Sponsor. Patients who discontinue trastuzumab emtansine can complete the duration of their study therapy with trastuzumab if appropriate based on toxicity considerations. Following discontinuation or completion of study treatment, patients will continue to be followed for efficacy and safety objectives until the end of the study.

Radiotherapy and/or hormonal therapy (for patients with hormone receptor-positive tumors) concurrent with study treatment should be administered if indicated based on the following guidelines:

Hormonal therapy (aromatase inhibitor, tamoxifen, etc.) should be initiated in patients with hormone receptor-positive disease at presentation.

For patients undergoing breast-conserving surgery, whole breast irradiation is required. Primary tumor bed boost can be administered according to local policy. Regional node irradiation is required if the patient presented at initial diagnosis with clinical T3 (except for T3N0) or T4 disease and/or with clinical N2 or N3 disease; it is recommended for T3N0 or if there is residual disease in lymph nodes.

For post-mastectomy patients, chest wall and regional node irradiation is required if the patient presented at initial diagnosis with clinical T3 (except for T3N0) or T4 disease and/or with clinical N2 or N3 disease; it is recommended for T3N0 or if there is residual disease in lymph nodes. For post-mastectomy patients who do not meet these criteria, radiotherapy is at the discretion of the investigator based on institutional standards.

A permuted-block randomization scheme will be used to ensure an approximate 1:1 allocation of patients to receive trastuzumab emtansine or trastuzumab with respect to the following stratification factors:

Clinical stage at presentation: inoperable (Stage T4N×M0 or T×N2-3M0) versus operable (Stages T1-3N0-1M0)

- Hormone receptor status: estrogen receptor (ER) or progesterone receptor (PgR) positive versus ER and PgR negative/unknown
- Preoperative HER2 targeted therapy: trastuzumab versus trastuzumab plus additional HER2 targeted agent(s)
- Pathologic nodal status evaluated after preoperative therapy: node positive versus node negative/not done Efficacy Outcome Measures Primary Efficacy Outcome Measures The primary efficacy outcome measures for this study are as follows:

The primary efficacy outcome measure is IDFS, defined as the time from randomization until the date of the first occurrence of any one of the following events:

- Ipsilateral invasive breast tumor recurrence (i.e., an invasive breast cancer involving the same breast parenchyma as the original primary lesion).
- Ipsilateral local-regional invasive breast cancer recurrence (i.e., an invasive breast cancer in the axilla, regional lymph nodes, chest wall and/or skin of the ipsilateral breast).
- Distant recurrence (i.e., evidence of breast cancer in any anatomic site—other than the 2 above-mentioned sites—that has either been histologically confirmed or clinically diagnosed as recurrent invasive breast cancer).
- Contralateral invasive breast cancer.
- Death attributable to any cause including breast cancer, non-breast cancer or unknown cause (but cause of death should be specified if at all possible).

Secondary Efficacy Outcome Measures

Secondary efficacy outcome measures include the following:

- IDFS including second primary non-breast cancer: defined the same way as IDFS for the primary endpoint but including second primary non-breast invasive cancer as an event (with the exception of non-melanoma skin cancers and carcinoma in situ [CIS] of any site)
- DFS: defined as the time between randomization and the date of the first occurrence of an IDFS event including second primary non-breast cancer event or contralateral or ipsilateral ductal carcinoma in situ (DCIS)
- OS: defined as the time from randomization to death due to any cause
- DRFI: defined as the time between randomization and the date of distant breast cancer recurrence Safety Outcome Measures Clinical and laboratory AEs will be reported according to the NCI CTCAE, Version 4.0. LVEF will be assessed using either echocardiogram (ECHO) or multiple-gated acquisition (MUGA).

Safety will be measured by determining the incidence, nature, and severity of AEs. The safety outcome measures are the following protocol-specific AEs:

- Incidence, type and severity of all AEs based on NCI CTCAE Version 4.0.
- Incidence, type, and severity of SAEs.
- Incidence and type of AEs leading to dose discontinuation, modification, or delay.
- Cause of death on study.
- Abnormal laboratory values.
- LVEF decreases.
- Cardiac events, defined as death from cardiac cause or severe CHF (NYHA Class III or IV) with a decrease in LVEF of ≥10 percentage points from baseline to an LVEF of <50%.

Patient Reported Outcome (PRO) Measures

The PRO measures for this study are as follows:

- Incidence of treatment-related symptoms and assessment of health-related quality of life (HRQOL) as measured using the EORTC QLQ-C30 questionnaire and QLQBR23 module.
- Assessment of health status as measured using the EuroQol EQ-5D™ questionnaire for health economic modeling.

Dosage, Administration, and Compliance

Trastuzumab Emtansine

Trastuzumab emtansine (T-DM1) will be administered on Day 1 of a 3-week cycle q3w at a dose of 3.6 mg/kg IV. If the timing coincides with a holiday that precludes administration, administration should be performed within 5 business days following the scheduled date. The total dose will be calculated based on the patient's weight on Day 1 of (or up to 3 days before) each cycle with no upper limit. Changes in weight of <10% from baseline do not require dose recalculation.

Trastuzumab emtansine doses can be reduced to as low as 2.4 mg/kg, according to the dose-modification guidelines. Dose delays of up to 42 days from the last administered dose are permitted.

The first infusion of trastuzumab emtansine will be administered over 90 minutes (±10 minutes). Infusions can be slowed or interrupted for patients experiencing infusion-associated symptoms. Vital signs must be assessed before and after dose administration. Following the initial dose, patients will be observed for at least 90 minutes for fever, chills, or other infusion-associated symptoms. If prior infusions were well tolerated (without any signs or symptoms of infusion reactions), subsequent doses of trastuzumab emtansine can be administered over 30 minutes (±10 minutes), with a minimum 30-minute observation period after infusion. Local health authority guidelines must be followed with regard to further observation and monitoring, if applicable. Premedication for nausea and infusion reactions (e.g., acetaminophen or other analgesics, antihistamines such as diphenhydramine, or corticosteroids) can be given at the investigator's discretion.

Trastuzumab

Trastuzumab will be administered on Day 1 of a 3-week cycle at a maintenance dose of 6 mg/kg IV. A loading dose of 8 mg/kg is required if >6 weeks have elapsed since the prior dose of trastuzumab. If the timing coincides with a holiday that precludes administration, administration should be performed within 5 business days following the scheduled date.

Infusion of trastuzumab should be performed in accordance with local guidelines and/or prescribing information.

Example 2—Results of Clinical Trial

Results of KATHERINE (NCT01772472/BO27938/NSABPB-50-I/GBG 77) phase III trial, which compared adjuvant trastuzumab emtansine (T-DM1) with trastuzumab in patients with HER2-positive early breast cancer and residual invasive disease after neoadjuvant chemotherapy and HER2 targeted therapy are provided in this Example.

Study Design

KATHERINE is a randomized, multicenter, open label phase 3 trial in which eligible patients were randomized to T-DM1 or trastuzumab as adjuvant therapy (FIG. 1).

Study Oversight

The study was designed by a steering committee consisting of members from the German Breast Group (GBG), The National Surgical Adjuvant Breast and Bowel Project (NS- ABP) Foundation, independent investigators, and the sponsor (F. Hoffmann-La Roche/Genentech), and conducted under the guidance of an independent data monitoring committee (IDMC). Data were collected by the sponsor using a platform held and managed by the NSABP Foundation. The prespecified interim analysis was reviewed by the IDMC, which recommended reporting the results. The recommendation and the interim analysis results were reviewed by the sponsor in collaboration with the study steering committee who concurred. The steering committee vouches for the completeness and accuracy of the data and analyses, and for the fidelity of the study to the protocol. The study was conducted in accordance with the amended Declaration of Helsinki and the protocol and was approved by the institutional review board at each participating center. All patients provided written informed consent.

Patients

Eligible patients had histologically confirmed, HER2-positive, non-metastatic, invasive primary breast cancer (T1-4, N0-3, M0) with pathologically documented residual invasive disease in the breast and/or axillary lymph nodes following neoadjuvant therapy and surgical resection. HER2 status was based on pretreatment biopsy samples and centrally confirmed prior to study enrollment. Patients had to have completed at least 6 cycles (16 weeks) of preoperative chemotherapy with at least 9 weeks of taxane-based therapy, and at least 9 weeks of trastuzumab therapy (shorter treatment durations were permitted for dose-dense regimens). Anthracyclines and additional HER2 targeted agents were permitted. Exclusion criteria included initial clinical stage T1a/bN0; gross residual disease at the resection margin; recurrent or progressive disease after preoperative systemic therapy; cardiopulmonary dysfunction including New York Heart Association class II or greater heart failure or a history of left ventricular ejection fraction reduction to less than 40% with prior trastuzumab; and prior cumulative exposure exceeding a doxorubicin 240 mg/m$^2$ equivalent.

HER2-positive status was defined as an immunohistochemistry score of 3+ and/or amplification of HER2 by in situ hybridization, defined as a ratio of 2.0 or greater for the number of HER2 gene copies to the number of signals for chromosome 17 copies based on local pathology of the primary tumor, according to American Society of Clinical Oncology/College of American Pathologists guidelines.

Treatment

Patients were randomized within 12 weeks of surgery using an interactive voice or web response system in a 1:1 ratio. A permuted block randomization scheme was used with stratification according to clinical stage at presentation (inoperable [tumor stage T4 or nodal stage N2 or N3 and metastasis stage M0] versus operable [tumor stage T1 to T3, nodal stage N0 or N1, and metastasis stage M0]); hormone receptor status per local laboratory (positive versus negative or unknown); preoperative HER2 targeted therapy (trastuzumab versus trastuzumab plus additional HER2 targeted agent[s]); and pathologic nodal status evaluated after neoadjuvant therapy (node positive versus node negative/not performed).

Patients received T-DM1 3.6 mg per kilogram of body weight or trastuzumab 6 mg per kilogram, each administered intravenously every 3 weeks for 14 cycles. A trastuzumab loading dose of 8 mg per kilogram was administered if more than 6 weeks had elapsed since the preceding trastuzumab dose. Patients who discontinued T-DM1 due to toxicity could complete 14 cycles of study treatment with trastuzumab at the investigator's discretion. Endocrine and radiation therapy were administered per institutional standards and the protocol.

Assessments

Reassessment for metastatic disease was not mandatory after neoadjuvant therapy and surgery prior to randomization. Assessments for disease recurrence occurred every 3 months for up to 2 years, every 6 months from 3 to 5 years, and annually from 6 to 10 years. Patients were assessed for toxicity prior to each dose of study drug. Left ventricular ejection fraction was assessed during the last week of cycle 2, every 4 cycles thereafter, at study drug completion, 3, 6, 12, 18, and 24 months, then annually to year 5.

Statistical Analysis

The primary end point was invasive-disease-free survival, defined as the time from randomization until the date of the first occurrence of an invasive-disease event: recurrence of ipsilateral invasive breast tumor, recurrence of ipsilateral locoregional invasive disease, a distant disease recurrence, contralateral invasive breast cancer, or death from any cause. The standardized definitions for efficacy end points (STEEP) includes second primary nonbreast cancer as an event for invasive-disease-free survival (Hudis J C O 2007); this definition was included as a secondary end point. Other secondary end points included disease-free survival, overall survival, distant recurrence-free survival, and safety.

A sample size of 1484 patients was planned, based on a requirement of 384 invasive-disease events to provide 80% power to detect a hazard ratio of 0.75 with a 2-sided significance level of 5% for the primary analysis. This calculation assumes 3-year invasive-disease-free survival rates of 75.6% (T-DM1) and 70.0% (trastuzumab). An interim analysis of invasive-disease-free survival was planned when approximately 267 (67%) of the targeted invasive-disease events had occurred, with an efficacy stopping boundary of $P<0.0124$ or an observed hazard ratio of 0.732 or less. The results of the interim analysis crossed the early reporting boundary.

The primary analysis was conducted on the intention-to-treat population. Rates of invasive-disease-free survival were compared between groups using a stratified log-rank test. The hazard ratio and its 95% confidence interval (CI) were estimated with a Cox proportional-hazards model. The 3-year event-free rates for each treatment group were estimated with the Kaplan-Meier method. Data from patients without a documented event were censored at the date the patient was last known to be alive and event-free.

The first interim overall survival analysis was planned for the time of the interim invasive-disease-free survival analysis if the interim invasive-disease-free survival analysis crossed the prespecified boundary. The overall type I error is controlled at 0.05 for the overall survival analysis using the Lan-DeMets alpha spending function with an O'Brien-Fleming boundary.

Results 1486 patients were enrolled and randomized (T-DM1, n=743; trastuzumab, n=743). Median duration of follow-up was approximately 41 months in the intention-to-treat population. Baseline characteristics were balanced between treatment arms (FIG. 2). Hormone-receptor-positive disease was present in 72.3% of patients. An anthracycline was received by 76.9% of patients, and an additional HER2 targeted therapy (usually pertuzumab) was administered as a component of neoadjuvant therapy in 19.5% of patients.

Efficacy

Figure 3:
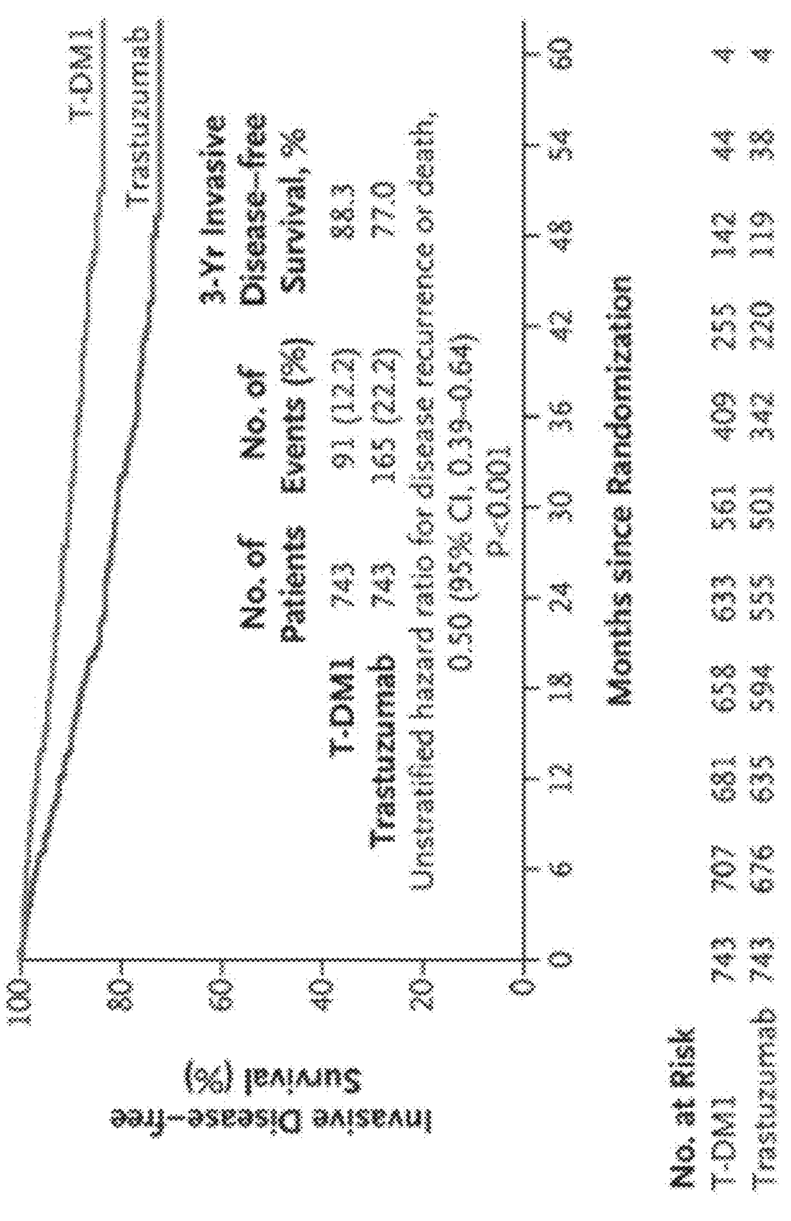
FIG. 3 depicts a Kaplan-Meier plot of invasive-disease-free survival. Invasive-disease-free survival was defined as the time from randomization until the date of the first occurrence of ipsilateral invasive breast tumor recurrence, ipsilateral locoregional invasive disease recurrence, distant disease recurrence, contralateral invasive breast cancer, or death from any cause. CI, denotes confidence interval; HR denotes hazard ratio.

The primary end point was met at this pre-planned interim analysis. Invasive-disease-free survival was statistically significantly improved in patients receiving T-DM1 compared to trastuzumab (hazard ratio, 0.50; 95% CI, 0.39 to 0.64; P<0.0001 (FIG. 3A). The 0.50 hazard ratio indicates that the T-DM1 monovalent adjuvant therapy provided a 50% reduction in the risk of invasive disease recurrence as compared to adjuvant therapy with trastuzumab.

Figure 4A:
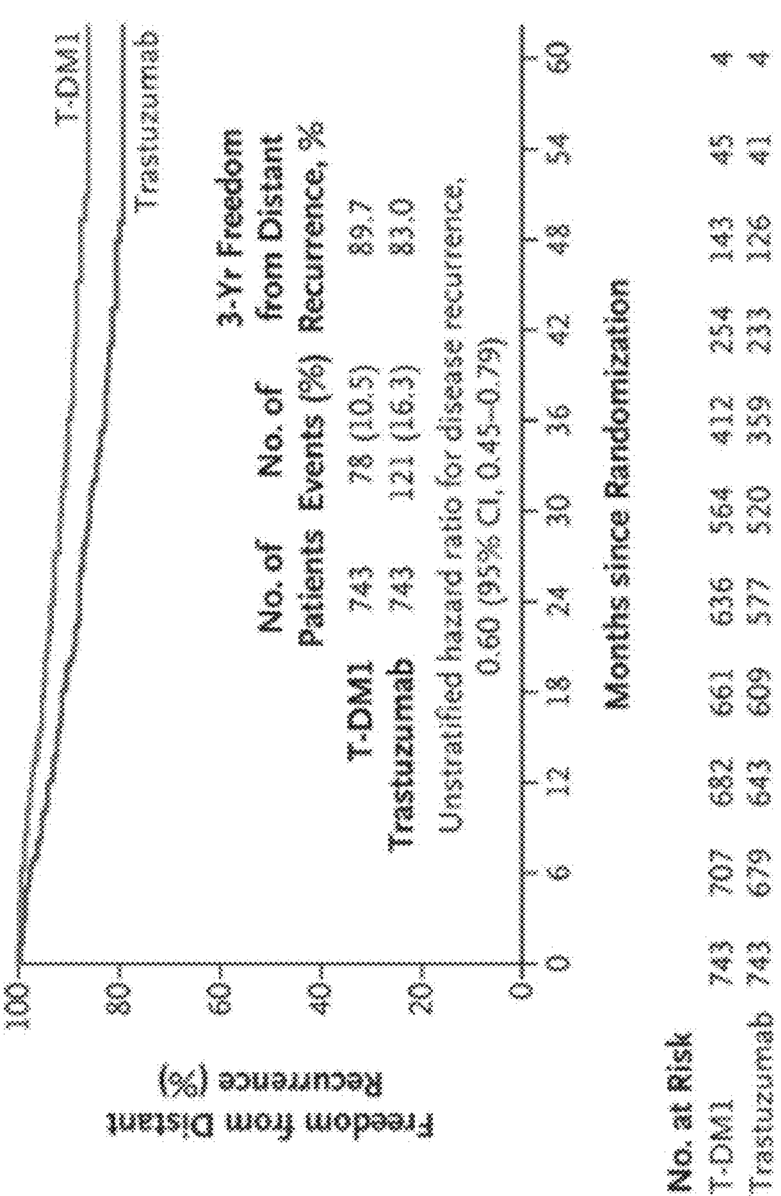
FIG. 4A depicts a Kaplan-Meier plot of distant recurrence, defined as evidence of breast cancer in any anatomical site—other than ipsilateral invasive breast tumor or recurrence of locoregional invasive breast cancer—that was either histologically confirmed or clinically diagnosed as recurrent invasive breast cancer. No statistical adjustments were made for multiple comparisons.

Invasive-disease-free survival events occurred in 91 patients (12.2%) receiving T-DM1 and 165 patients (22.2%) receiving trastuzumab. The 3-year invasive-disease-free survival estimates were 88.3% (T-DM1) and 77.0% (trastuzumab). Distant recurrence as the first invasive-disease event occurred in 78 patients (10.5%) receiving T-DM1 and 118 patients (15.9%) receiving trastuzumab (FIGS. 4A, 4B).

The risk of distant recurrence was lower in the T-DM1 group than in the trastuzumab group (hazard ratio, 0.60; 95% CI, 0.45 to 0.79 (FIG. 5). The 0.60 hazard ratio indicates that the T-DM1 monovalent adjuvant therapy provided a 40% reduction in the risk of distant recurrence as compared to adjuvant trastuzumab.

Including second primary nonbreast cancer as an invasive-disease event increased the number of patients with an event to 95 (12.8%) in the T-DM1 group and 167 (22.5%) in the trastuzumab group; the difference in invasive-disease-free survival remained in favor of T-DM1 (hazard ratio, 0.51; 95% CI, 0.40 to 0.66; P<0.0001) (FIG. 5).

Figure 6A:
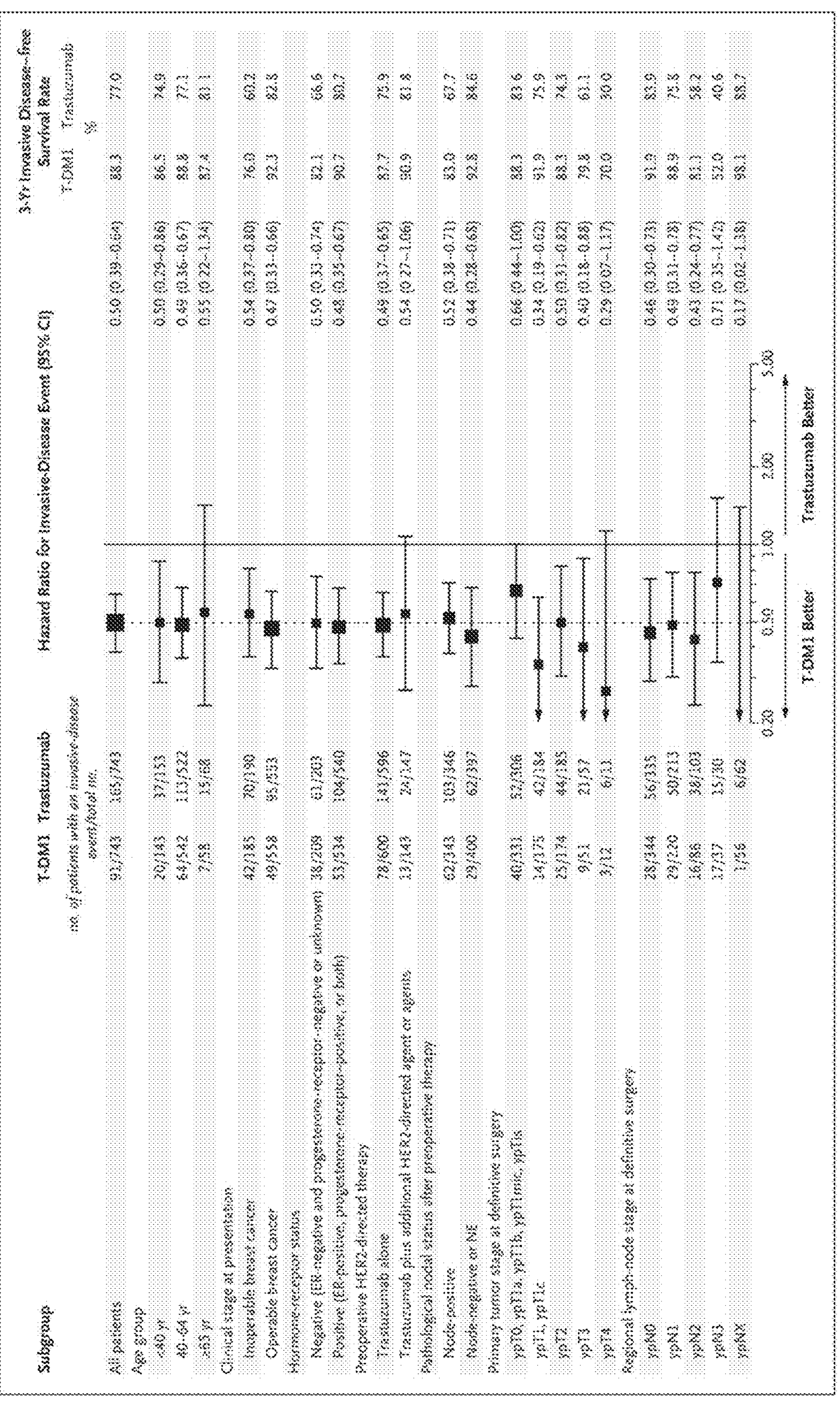
FIGS. 6A and 6B depict a Forest plot of invasive-disease-free survival. CI, denotes confidence interval. Hormone receptor negative denotes estrogen-receptor (ER)-negative and progesterone-receptor (PgR)-negative; hormone receptor positive denotes ER-positive, PgR-positive, or both. HER2 denotes human epidermal growth factor receptor. ICH denotes immunohistochemistry. IDFS denotes invasive disease-free survival. ISH denotes in situ hybridization.
Figure 6B:
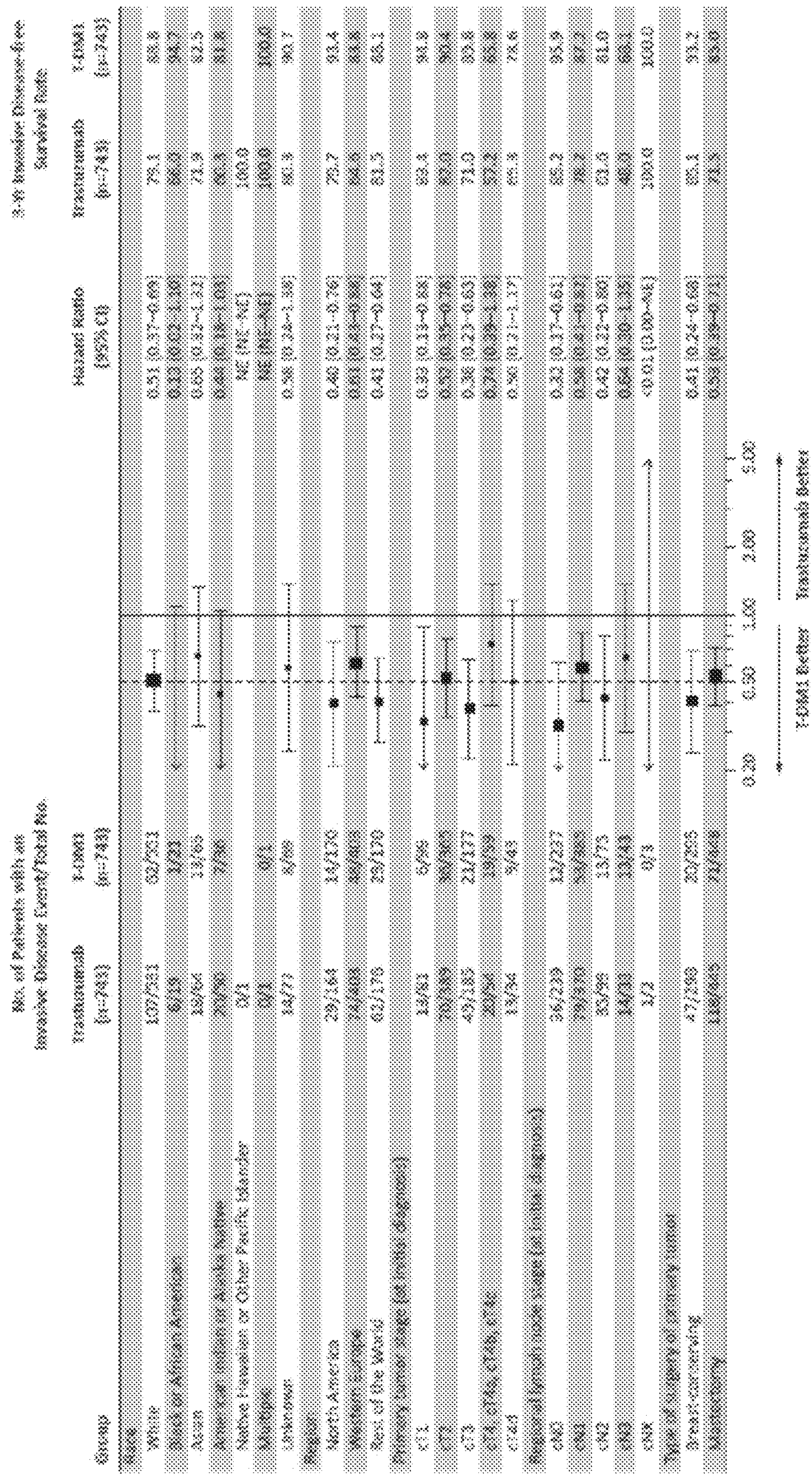

The subgroup analysis of invasive-disease-free survival revealed a consistent benefit for T-DM1 across patient subgroups (FIGS. 6A and 6B), including those with hormone-receptor-positive disease (hazard ratio, 0.48; 95% CI, 0.35 to 0.67), hormone-receptor-negative disease (hazard ratio, 0.50; 95% CI, 0.33 to 0.74), pathological node positive status evaluated after preoperative therapy (hazard ratio, 0.52; 95% CI, 0.38 to 0.71), node-negative status (hazard ratio, 0.44; 95% CI, 0.28 to 0.68), patients with small residual disease (ypT0/ypT1a/ypT1b/ypTmic/ypTis (hazard ratio, 0.66; 95% CI, 0.44 to 1.00), neoadjuvant trastuzumab alone (hazard ratio, 0.49; 95% CI, 0.37 to 0.65), and neoadjuvant trastuzumab plus any additional HER2 targeted therapy (hazard ratio, 0.54; 95% CI, 0.27 to 1.06). Similar results were observed when comparing T-DM1 to trastuzumab in patients who received neoadjuvant trastuzumab alone or neoadjuvant trastuzumab plus pertuzumab. A benefit of adjuvant T-DM1 relative to adjuvant trastuzumab was observed irrespective of neoadjuvant HER2 targeted therapy. Among patients who received neoadjuvant trastuzumab with chemotherapy, invasive-disease events occurred in 78 patients in the T-DM1 group and 141 patients in the adjuvant trastuzumab group (hazard ratio, 0.49; 95% CI, 0.37 to 0.65). Among patients who received neoadjuvant trastuzumab plus a second HER2 targeted therapy with chemotherapy, invasive-disease events occurred in 13 patients in the T-DM1 group and 24 patients in the adjuvant trastuzumab group (hazard ratio, 0.54; 95% CI, 0.27 to 1.06). Pertuzumab was the second therapy in 93.8% of patients who received a second neoadjuvant HER2 targeted agent, and in this group, invasive-disease events occurred in 12 patients in the T-DM1 group and 24 patients in the adjuvant trastuzumab group (hazard ratio, 0.50; 95% CI, 0.25 to 1.00). (FIG. 7). Other HER2 targeted therapies used as the second therapy included lapatinib, neratinib, dacomitinib, and afatinib.

Figure 8:
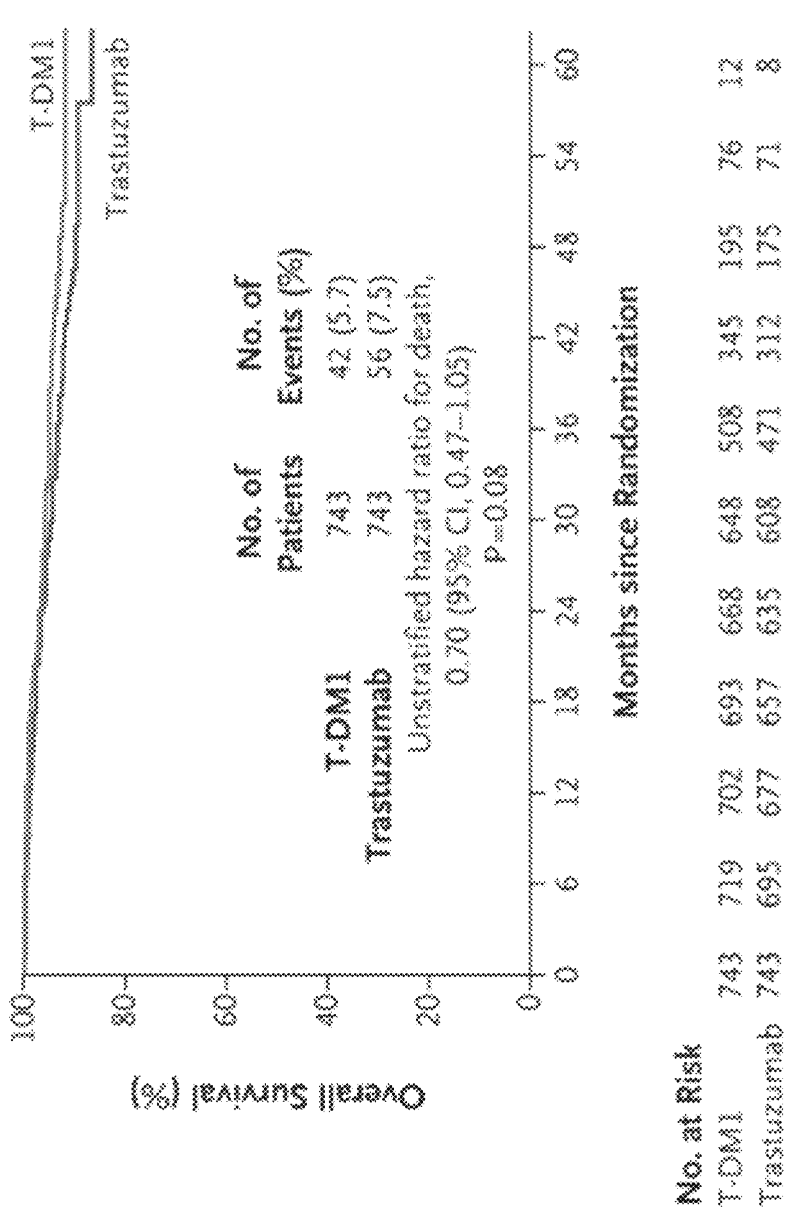
FIG. 8 depicts a Kaplan-Meier plot of overall survival of the patient population.

With 98 deaths occurring (42 patients (5.7%), T-DM1; 56 patients (7.5%), trastuzumab), the overall survival analysis is not mature and did not cross the boundary (hazard ratio 0.70; 95% CI, 0.47 to 1.05; P=0.08) (FIGS. 5 and 8). The numbers of patients who died without a prior invasive-disease event were 2 (T-DM1) and 3 (trastuzumab).

Safety

A total of 1460 patients were analyzed for safety (n=740, T-DM1; n=720, trastuzumab). The planned 14 cycles of randomized study treatment were completed by 70.9% (T-DM1) and 78.7% (trastuzumab) of patients. Sixty-five patients discontinued T-DM1 and continued on trastuzumab to complete a total of 14 cycles of treatment. The most common grade 3 or higher adverse events were decreased platelet count and hypertension in the T-DM1 arm, and hypertension and radiation skin injury in the trastuzumab arm. Serious adverse events occurred in 94 patients (12.7%) receiving T-DM1 and 59 patients (8.2%) receiving trastuzumab. Adverse events leading to randomized treatment discontinuation occurred in 18.0% of T-DM1-treated patients and 2.1% of trastuzumab-treated patients. Two fatal adverse events occurred, one in each arm, consisting of intracranial hemorrhage and encephalitis.

Radiation pneumonitis of any grade occurred in 11 T-DM1-treated patients (1.5%) and 5 trastuzumab-treated patients (0.7%). Increased aminotransferase levels of any grade occurred more frequently with TDM-1 (alanine aminotransferase, 23.1%; aspartate aminotransferase, 28.4%) than with trastuzumab (alanine aminotransferase, 5.7%; aspartate aminotransferase, 5.6%). These increases led to T-DM1 discontinuation in 1.5% of patients (alanine aminotransferase) and 1.6% of patients (aspartate aminotransferase). No patient in the trastuzumab arm discontinued treatment due to aminotransferase increases. Two adjudicated cases of nodular regenerative hyperplasia occurred, both in the T-DM1 arm.

Discussion

In the KATHERINE trial, adjuvant treatment with T-DM1 provided a 50% reduction in the risk of invasive disease recurrence or death compared to adjuvant trastuzumab in patients with HER2-positive early breast cancer and residual invasive disease after neoadjuvant chemotherapy plus HER2 targeted therapy. Subgroup analyses showed a consistent benefit, irrespective of hormone-receptor status, the extent of residual disease at surgery, single or dual HER2 targeted therapy in the neoadjuvant regimen, and baseline characteristics of the patients. Importantly, fewer patients receiving T-DM1 experienced distant recurrence as their first invasive disease event (10.5%) compared to trastuzumab (15.9%). These results represent a major treatment advance in this high-risk population.

Currently, choice of adjuvant treatment for patients with residual invasive disease after neoadjuvant treatment is based on data extrapolated from trials in other settings. APHINITY demonstrated a disease-free survival advantage (hazard ratio, 0.81; 95% CI, 0.66 to 1.00; P=0.045) for adjuvant chemotherapy plus dual HER2-blockade with pertuzumab plus trastuzumab compared to chemotherapy plus trastuzumab alone among node-positive or high-risk node-negative patients (von Minckwitz NEJM 2017). Despite these data, the benefit of additional dual blockade adjuvant therapy after neoadjuvant dual blockade plus chemotherapy remained unknown. Subgroup analysis from KATHERINE suggests that T-DM1 can be the appropriate choice in patients with residual disease and provides evidence that switching to T-DM1 results in benefit in such patients who received a neoadjuvant regimen of dual HER2 blockade plus trastuzumab and chemotherapy (hazard ratio, 0.54; 95% CI, 0.27 to 1.06). This benefit is consistent with that observed in patients receiving preoperative chemotherapy plus trastuzumab (hazard ratio, 0.49; 95% CI, 0.37 to 0.65).

The overall safety profile of T-DM1 was generally consistent with that observed in the metastatic setting, with expected increases in adverse events associated with T-DM1 compared to trastuzumab alone.

REFERENCES

Cortazar P, Zhang L, Untch M, et al. Pathological complete response and long-term clinical benefit in breast cancer: the CTNeoBC pooled analysis. Lancet 2014; 384:164-72.

de Azambuja E, Holmes A P, Piccart-Gebhart M, et al. Lapatinib with trastuzumab for HER2-positive early breast cancer (NeoALTTO): survival outcomes of a randomised, open-label, multicentre, phase 3 trial and their association with pathological complete response. Lancet Oncol 2014; 15:1137-46.

Diéras V, Miles D, Verma S, et al. Trastuzumab emtansine versus capecitabine plus lapatinib in patients with previously treated HER2-positive advanced breast cancer (EMILIA): a descriptive analysis of final overall survival results from a randomised, open-label, phase 3 trial. Lancet Oncol 2017; 18:732-742.

Diéras V, Harbeck N, Budd G T, et al. Trastuzumab emtansine in human epidermal growth factor receptor 2-positive metastatic breast cancer: an integrated safety analysis. J Clin Oncol. 2014; 32(25):2750-2757.

Egloff H, Kidwell K M, Schott A. Ado-trastuzumab emtansine-induced pulmonary toxicity: a single-institution retrospective review. Case Rep Oncol. 2018; 11:527-533.

Gianni L, Eiermann W, Semiglazov V, et al. Neoadjuvant and adjuvant trastuzumab in patients with HER2-positive locally advanced breast cancer (NOAH): follow-up of a randomised controlled superiority trial with a parallel HER2-negative cohort. Lancet Oncol 2014; 15:640-7.

Gianni L, Pienkowski T, Im Y H, et al. 5-year analysis of neoadjuvant pertuzumab and trastuzumab in patients with locally advanced, inflammatory, or early-stage HER2-positive breast cancer (NeoSphere): a multicentre, open-label, phase 2 randomised trial. Lancet Oncol 2016; 17:791-800.

Gullo G, Walsh N, Fennelly D, et al. Impact of timing of trastuzumab initiation on long-term outcome of patients with early-stage HER2-positive breast cancer: the "one thousand HER2 patients" project. Br J Cancer 2018; 119:374-380.

Hudis C A, Barlow W E, Costantino J P, et al. Proposal for standardized definitions for efficacy end points in adjuvant breast cancer trials: the STEEP system. J Clin Oncol 2007; 25:2127-32.

Hurvitz S A, Martin M, Symmans W F, et al. Neoadjuvant trastuzumab, pertuzumab, and chemotherapy versus trastuzumab emtansine plus pertuzumab in patients with HER2-positive breast cancer (KRISTINE): a randomised, open-label, multicentre, phase 3 trial. Lancet Oncol 2018; 19:115-126.

Junttila T T, Li G, Parsons K, Phillips G L, et al. Trastuzumab-DM1 (T-DM1) retains all the mechanisms of action of trastuzumab and efficiently inhibits growth of lapatinib insensitive breast cancer. Breast Cancer Res Treat 2011; 128:347-56.

Kadcyla (package insert). South San Francisco, CA: Genentech, Inc.; September 2018.

Krop I E, Kim S B, Gonzalez-Martin A, et al. Trastuzumab emtansine versus treatment of physician's choice for pretreated HER2-positive advanced breast cancer (TH3RESA): a randomised, open-label, phase 3 trial. Lancet Oncol 2014; 15:689-99.

Krop I E, Kim S B, Martin A G, et al. Trastuzumab emtansine versus treatment of physician's choice in patients with previously treated HER2-positive metastatic breast cancer (TH3RESA): final overall survival results from a randomised open-label phase 3 trial. Lancet Oncol 2017; 18:743-754.

Krop I E, Suter™, Dang C T, et al. Feasibility and cardiac safety of trastuzumab emtansine after anthracycline-based chemotherapy as (neo)adjuvant therapy for human epidermal growth factor receptor 2-positive early-stage breast cancer. J Clin Oncol 2015; 33:1136-42.

Lewis Phillips G D, Li G, Dugger D L, et al. Targeting HER2-positive breast cancer with trastuzumab-DM1, an antibody-cytotoxic drug conjugate. Cancer Res 2008; 68:9280-90.

Lindstrom L S, Karlsson E, Wilking U M, et al. Clinically used breast cancer markers such as estrogen receptor, progesterone receptor, and human epidermal growth factor receptor 2 are unstable throughout tumor progression. J Clin Oncol 2012; 30:2601-2608.

Martin M, Holmes F A, Ejlertsen B, et al. Neratinib after trastuzumab-based adjuvant therapy in HER2-positive breast cancer (ExteNET): 5-year analysis of a randomised, double-blind, placebo-controlled, phase 3 trial. Lancet Oncol 2017; 18:1688-1700.

Masuda N, Lee S J, Ohtani S, et al. Adjuvant capecitabine for breast cancer after preoperative chemotherapy. N Engl J Med 2017; 376:2147-2159.

National Comprehensive Cancer Network. NCCN clinical practice guidelines in oncology: breast cancer version 1.2018.

Perez E A, Barrios C, Eiermann W, et al. Trastuzumab emtansine with or without pertuzumab versus trastuzumab plus taxane for human epidermal growth factor receptor 2-positive, advanced breast cancer: primary results from the phase III MARIANNE study. J Clin Oncol 2017; 35:141-148.

Promberger R, Dubsky P, Mittlbock M, et al. Postoperative CMF does not ameliorate poor outcomes in women with residual invasive breast cancer after neoadjuvant epirubicin/docetaxel chemotherapy. Clin Breast Cancer 2015; 15:505-11.

Schneeweiss A, Chia S, Hickish T, et al. Long-term efficacy analysis of the randomised, phase II TRYPHAENA cardiac safety study: Evaluating pertuzumab and trastuzumab plus standard neoadjuvant anthracycline-containing and anthracycline-free chemotherapy regimens in patients with HER2-positive early breast cancer. Eur J Cancer 2018; 89:27-35.

Senkus E, Kyriakides S, Ohno S, et al. Primary breast cancer: ESMO clinical practice guidelines for diagnosis, treatment and follow-up. Ann Oncol 2015; 26(Suppl 5):v8-30.

Untch M, Fasching P A, Konecny G E, et al. Pathologic complete response after neoadjuvant chemotherapy plus trastuzumab predicts favorable survival in human epidermal growth factor receptor 2-overexpressing breast cancer: results from the TECHNO trial of the AGO and GBG study groups. J Clin Oncol 2011; 29:3351-7.

Verma S, Miles D, Gianni L, et al. Trastuzumab emtansine for HER2-positive advanced breast cancer. N Engl J Med 2012; 367:1783-91.

von Minckwitz G, Procter M, de Azambuja E, et al. Adjuvant pertuzumab and trastuzumab in early HER2-positive breast cancer. N Engl J Med 2017; 377:122-131.

Yoshida A, Hayashi N, Suzuki K, Takimoto M, Nakamura S, Yamauchi H. Change in HER2 status after neoadjuvant chemotherapy and the prognostic impact in patients with primary breast cancer. J Surg Oncol 2017; 116:1021-1028.

von Minckwitz G, et al., Trastuzumab Emtansine for Residual Invasive HER2-Positive Breast Cancer. N Engl J Med 2019:380:617-628.

The foregoing description is considered as illustrative only of the principles of the present disclosure. Further, since numerous modifications and changes will be readily apparent to those skilled in the art, it is not desired to limit the present disclosure to the exact construction and process shown as described above. Accordingly, all suitable modifications and equivalents can be considered to fall within the scope of the present disclosure as defined by the claims that follow.

I claim:

1. A method of adjuvant therapy comprising administering to a patient with HER2-positive early breast cancer a therapeutically effective amount of trastuzumab emtansine (T-DM1) as a monotherapy wherein the initial administration occurs over about 80 minutes to about 100 minutes and subsequent administrations occur over about 20 minutes to about 40 minutes, and wherein the patient has residual disease present in a breast and/or axillary lymph node after a pre-operative systemic treatment, wherein the pre-operative systemic treatment comprises a HER2 targeted therapy and a taxane.

2. The method of claim 1, wherein the HER2 targeted therapy comprises trastuzumab.

3. The method of claim 1, wherein the patient is administered T-DM1 at a dose of 3.6 mg/kg every 3 weeks.

4. The method of claim 1, wherein the adjuvant therapy substantially increases invasive disease-free survival (IDFS) as compared to adjuvant therapy with trastuzumab.

5. The method of claim 1, wherein the adjuvant therapy provides a 50% reduction in the risk of invasive disease recurrence as compared to adjuvant therapy with trastuzumab.

6. The method of claim 1, wherein the adjuvant therapy leads to a decrease in distant recurrence as compared to adjuvant therapy with trastuzumab.

7. The method of claim 1, wherein the adjuvant therapy provides a 40% reduction in the risk of distant recurrence as compared to adjuvant trastuzumab.

8. A method for the treatment of breast cancer in a patient with HER2-positive early breast cancer who has residual disease in the breast or axillary lymph nodes after neoadjuvant therapy with a taxane and a HER2 targeted therapy, the method comprising:

(i) removing all clinically evident tumor cells in the breast and axillary lymph nodes by definitive surgery; and (ii) subjecting the patient to monotherapy adjuvant therapy with a therapeutically effective amount of trastuzumab emtansine (T-DM1) wherein the initial administration occurs over about 80 minutes to about 100 minutes and subsequent administrations occur over about 20 minutes to about 40 minutes.

9. The method of claim 8, wherein the HER2 targeted therapy comprises trastuzumab.

10. A method for the treatment of HER2-positive early breast cancer in a patient with residual disease present in a breast and/or axillary lymph node following neoadjuvant therapy, the method comprising administering to the patient a therapeutically effective amount of trastuzumab emtansine (T-DM1) after the patient is subjected to definitive surgery wherein the initial administration occurs over about 80 minutes to about 100 minutes and subsequent administrations occur over about 20 minutes to about 40 minutes, wherein the neoadjuvant therapy comprises a HER2 targeted therapy and a taxane.

11. The method of claim 10, wherein the method does not comprise prior or concurrent adjuvant treatment with chemotherapy.

12. The method of claim 10, wherein the treatment substantially increases invasive disease-free survival (IDFS) as compared to adjuvant treatment with trastuzumab.

13. The method of claim 10, wherein the treatment leads to a decrease in distant recurrence as compared to adjuvant treatment with trastuzumab.

14. A method for reducing the risk of cancer recurrence in a patient with HER2-positive early breast cancer who has residual disease in the breast or axillary lymph nodes, comprising administering to the patient a therapeutically effective amount of trastuzumab emtansine (T-DM1), wherein the initial administration occurs over about 80 minutes to about 100 minutes and subsequent administrations occur over about 20 minutes to about 40 minutes, and wherein the patient did not achieve pathologic complete response with neoadjuvant therapy and the patient had definitive surgery prior to the administering of T-DM1, wherein the neoadjuvant therapy comprises a HER2 targeted therapy and a taxane.

15. The method of claim 14, wherein the method does not comprise prior or concurrent adjuvant treatment with chemotherapy.

16. The method of claim 14, wherein the treatment substantially increases invasive disease-free survival (IDFS) as compared to adjuvant treatment with trastuzumab.

17. The method of claim 14, wherein the treatment leads to a decrease in distant recurrence as compared to adjuvant treatment with trastuzumab.

18. The method of claim 14, wherein the T-DM1 provides a 50% reduction in the risk of invasive disease recurrence as compared to adjuvant therapy with trastuzumab.

19. The method of claim 1, wherein the T-DM1 administration provides a 40% reduction in the risk of distant recurrence as compared to adjuvant trastuzumab.

* * * * *